United States Patent
Stewart et al.

(10) Patent No.: US 9,737,376 B2
(45) Date of Patent: Aug. 22, 2017

(54) ECCENTRIC DENTAL IMPLANT SYSTEM

(71) Applicant: Grant Dental Technology Corporation, Colorado Springs, CO (US)

(72) Inventors: Duncan Howard Stewart, Colorado Springs, CO (US); Douglas James Brooke, Colorado Springs, CO (US); Earl Wayne Simmons, Colorado Springs, CO (US); James Grant, Colorado Springs, CO (US)

(73) Assignee: Grant Dental Technology Corporation, Colorado Springs, CO (US)

( * ) Notice: Subject to any disclaimer, the term of this patent is extended or adjusted under 35 U.S.C. 154(b) by 0 days.

(21) Appl. No.: 14/642,565

(22) Filed: Mar. 9, 2015

(65) Prior Publication Data
US 2015/0250564 A1 Sep. 10, 2015

Related U.S. Application Data

(60) Provisional application No. 61/949,908, filed on Mar. 7, 2014.

(51) Int. Cl.
| | | |
|---|---|---|
| *A61C 8/00* | (2006.01) | |
| *A61C 3/03* | (2006.01) | |
| *A61C 1/08* | (2006.01) | |
| *A61C 1/18* | (2006.01) | |

(52) U.S. Cl.
CPC ............. *A61C 3/03* (2013.01); *A61C 1/084* (2013.01); *A61C 8/0025* (2013.01); *A61C 8/0063* (2013.01); *A61C 8/0089* (2013.01); *A61C 1/18* (2013.01)

(58) Field of Classification Search
CPC .. A61C 3/03; A61C 1/084; A61C 1/18; A61C 8/00; A61C 8/0024; A61C 8/0025; A61C 8/005; A61C 8/0059; A61C 8/0063; A61C 8/0069; A61C 8/0074; A61C 8/0089
USPC .......................................... 433/174, 173, 76
See application file for complete search history.

(56) References Cited

U.S. PATENT DOCUMENTS

| | | | |
|---|---|---|---|
| 4,086,701 A | 5/1978 | Kawahara et al. | |
| 4,713,003 A | 12/1987 | Symington et al. | |
| 4,988,297 A | 1/1991 | Lazzara et al. | |
| 5,018,970 A | 5/1991 | Stordahl | |

(Continued)

FOREIGN PATENT DOCUMENTS

CA 2732001 11/2009

OTHER PUBLICATIONS

International Search Report and Written Opinion of PCT/US2011/022737 mailed Mar. 23, 2011, 9 pages.

(Continued)

*Primary Examiner* — Pedro Philogene
*Assistant Examiner* — David C Comstock
(74) *Attorney, Agent, or Firm* — Kilpatrick Townsend & Stockton LLP

(57) ABSTRACT

A dental implant whereby an osteotomy cavity is formed in jawbone and then a base member of the implant is positioned into the cavity. The base member serves as a platform to secure an abutment member of the implant that in turn receives a dental restoration, such as a crown or denture.

21 Claims, 50 Drawing Sheets

(56) References Cited

U.S. PATENT DOCUMENTS

| | | | | |
|---|---|---|---|---|
| 5,022,860 A | * | 6/1991 | Lazzara | A61C 8/0022 433/174 |
| 5,040,982 A | | 8/1991 | Stefan-Dogar | |
| 5,135,395 A | * | 8/1992 | Marlin | A61C 8/0048 433/173 |
| 5,297,963 A | | 3/1994 | Dafatry | |
| 5,492,471 A | | 2/1996 | Singer | |
| 5,513,989 A | | 5/1996 | Crisio | |
| 5,564,925 A | | 10/1996 | Shampanier | |
| 5,571,015 A | | 11/1996 | Siegmund | |
| 5,591,029 A | | 1/1997 | Zuest | |
| 5,810,592 A | | 9/1998 | Daftary | |
| 6,068,479 A | | 5/2000 | Kwan | |
| 6,120,292 A | | 9/2000 | Buser et al. | |
| 6,168,436 B1 | | 1/2001 | O'Brien | |
| 6,250,922 B1 | | 6/2001 | Bassett et al. | |
| 6,287,117 B1 | | 9/2001 | Niznick | |
| 6,436,103 B1 | | 8/2002 | Suddaby | |
| 6,454,569 B1 | | 9/2002 | Hollander et al. | |
| 6,537,069 B1 | | 3/2003 | Simmons, Jr. | |
| 6,843,653 B2 | | 1/2005 | Carlton | |
| 6,863,529 B2 | | 3/2005 | Strong et al. | |
| 7,056,117 B2 | | 6/2006 | Simmons, Jr. | |
| 7,097,451 B2 | | 8/2006 | Tang | |
| 7,101,177 B2 | | 9/2006 | Lin | |
| 7,104,991 B2 | | 9/2006 | Dixon et al. | |
| 7,806,685 B1 | | 10/2010 | Grant | |
| 8,231,388 B2 | | 7/2012 | Grant | |
| 8,287,278 B2 | | 10/2012 | Grant | |
| 8,562,344 B2 | | 10/2013 | Grant | |
| 8,740,616 B2 | | 6/2014 | Grant | |
| 2002/0076673 A1 | | 6/2002 | Wagner et al. | |
| 2003/0180686 A1 | | 9/2003 | Simmons, Jr. | |
| 2004/0265781 A1 | | 12/2004 | Coatoam | |
| 2005/0019730 A1 | | 1/2005 | Gittleman | |
| 2005/0202368 A1 | * | 9/2005 | Ganley | A61C 8/005 433/173 |
| 2006/0014120 A1 | | 1/2006 | Sapian | |
| 2006/0093988 A1 | | 5/2006 | Swaelens et al. | |
| 2008/0118892 A1 | | 5/2008 | Adams | |
| 2008/0124675 A1 | | 5/2008 | Adams | |
| 2009/0081612 A1 | | 3/2009 | Jorneus et al. | |
| 2009/0226857 A1 | | 9/2009 | Grant | |
| 2009/0258329 A1 | | 10/2009 | Adams | |
| 2010/0112522 A1 | | 5/2010 | Kwon | |
| 2010/0159419 A1 | | 6/2010 | Grant | |
| 2010/0266987 A1 | | 10/2010 | Ford | |
| 2010/0330534 A1 | | 12/2010 | Hyun | |
| 2011/0118742 A1 | | 5/2011 | Hulliger et al. | |
| 2011/0151408 A1 | | 6/2011 | Grant | |
| 2011/0200969 A1 | * | 8/2011 | Schroering | A61C 8/0018 433/174 |
| 2012/0196250 A1 | | 8/2012 | Grant | |
| 2014/0272793 A1 | | 9/2014 | Grant et al. | |

OTHER PUBLICATIONS

International Preliminary Report on Patentability for PCT/US2011/022737 issued Jul. 31, 2013, 2 pages.

International Search Report and Written Opinion of PCT/US2012/063792 mailed on Jan. 31, 2013, 11 pages.

* cited by examiner

100b

102a

102b

102b

104b

104a

104b

106a

106b

106b

108b

108b

108a

108b

ECCENTRIC DENTAL IMPLANT SYSTEM

CROSS-REFERENCE TO RELATED APPLICATION

This application claims the benefit of U.S. Prov. Pat. App. Ser. 61/949,908, filed 7 Mar. 2014, the entirety of which is hereby incorporated by reference for all purposes.

BACKGROUND

Implants are a popular means of or for replacing a tooth. Due to their relatively low maintenance and durability, people increasingly prefer implants to bridges or dentures. Nevertheless, there remain significant complications that are the result of using a round implant in a jawbone space that formerly had a non-round or eccentric tooth, and is therefore undersized in one or more horizontal dimensions in relation to the tooth it would replace. These complications include food impaction, bacteria collection, and excessive stress on bone and implant components.

SUMMARY

A dental implant that includes or comprises an eccentrically-shaped abutment member, an implant screw, and an eccentrically-shaped base member. In practice, the base member is fitted to or positioned within an eccentrically-shaped osteotomy box or cavity formed within jawbone. Following the folding back of tissue and the drilling of a pilot hole within the jawbone, the implant screw is positioned through a central passage formed within the base member and then is torqued into place to rigidly secure the base member to the jawbone. Then, the abutment member is fitted to the base member. In some examples, the central passage formed within the base member is tapered to match a taper of the head of the implant screw. In so doing, a friction fit or cold weld is formed between the implant screw and the base member. Additionally, in some examples, the central passage formed within the base member includes an internal thread that is complementary to an external thread of the implant screw. In so doing, the friction fit or cold weld formed between the implant screw and the base member is securely held in place. Although not so limited, and appreciation of the various aspects of the present disclosure may be gained from the following discussion in connection with the drawings.

DESCRIPTION OF THE DRAWINGS

A further understanding of the aspects of the disclosure may be realized by reference to the following figures. In the figures, similar components or features may have the same reference label. Further, various components of the same type may be distinguished by immediately following the reference label with a second label that distinguishes among the similar components. When only the first reference label is used in the specification, the description is applicable to any one of the similar components having the same first reference label irrespective of whether the second reference label is recited.

DETAILED DESCRIPTION

Figure 1A:
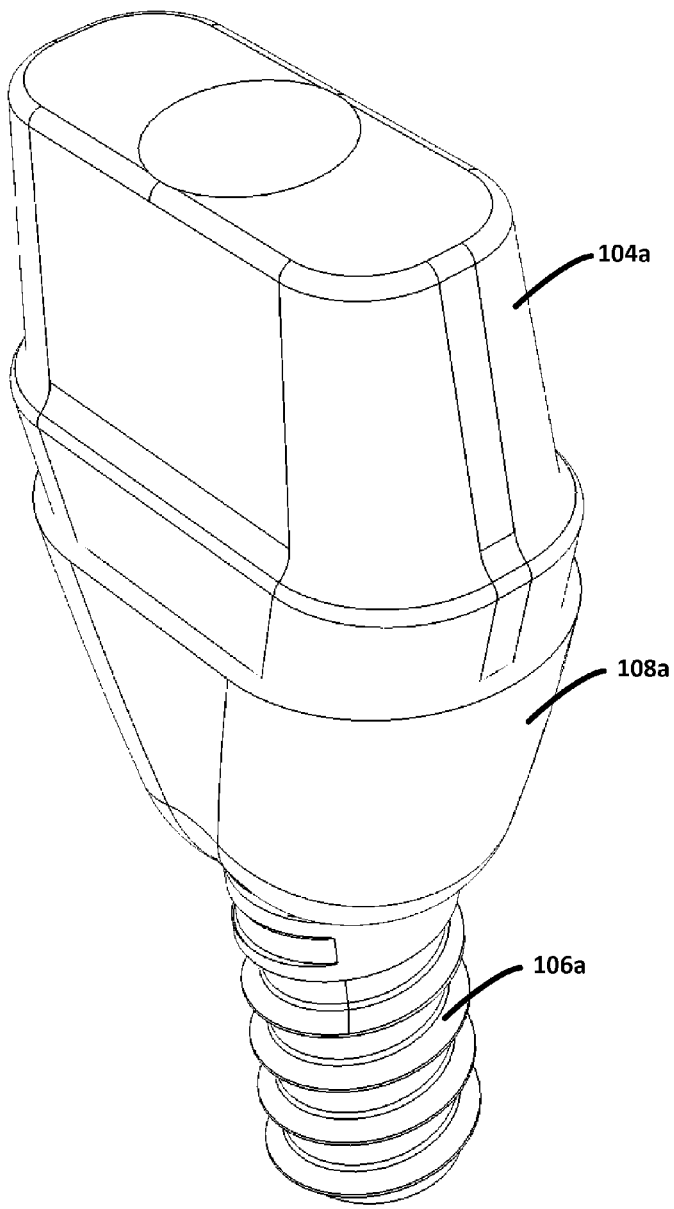
FIGS. 1A-B each show a perspective view of an example assembled dental implant.
Figure 1B:
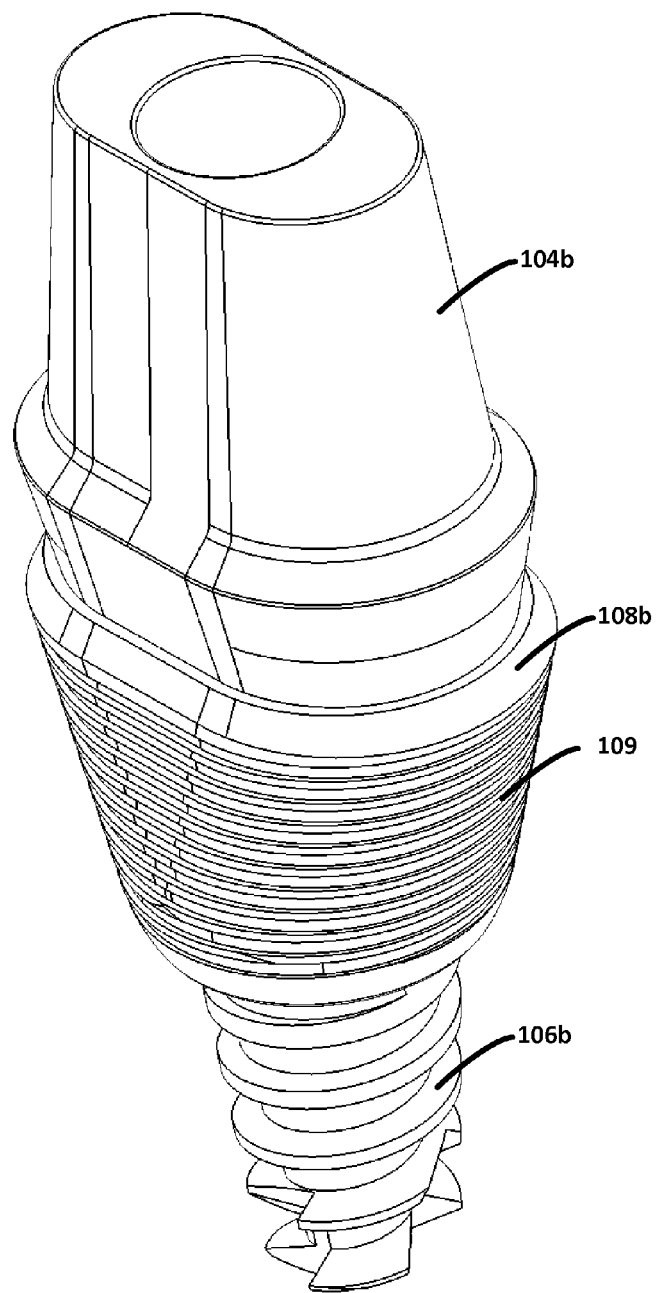
Figure 2A:
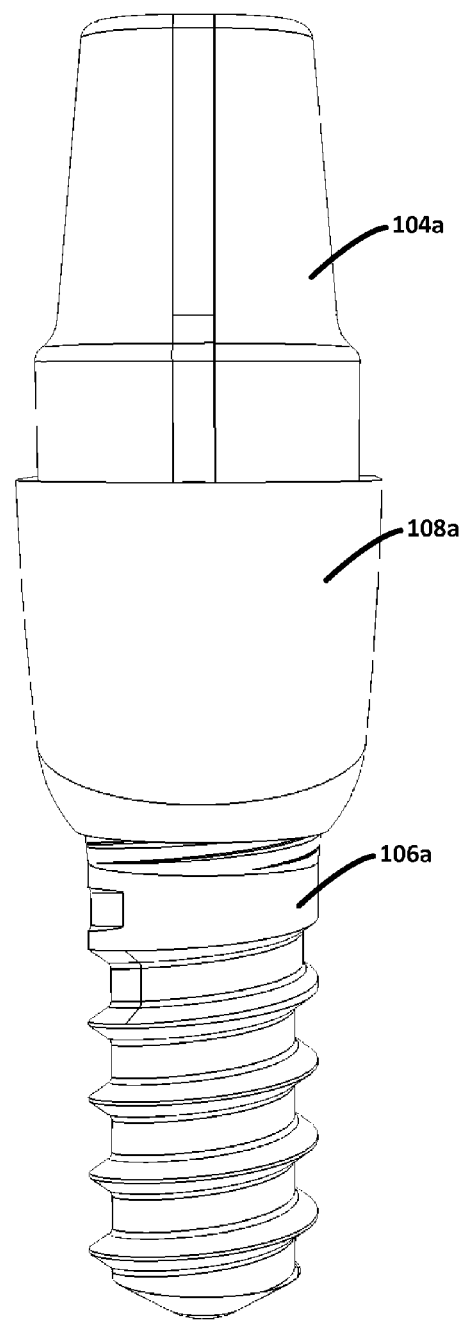
FIGS. 2A-B show a side view of the implant of FIGS. 1A-B.
Figure 2B:
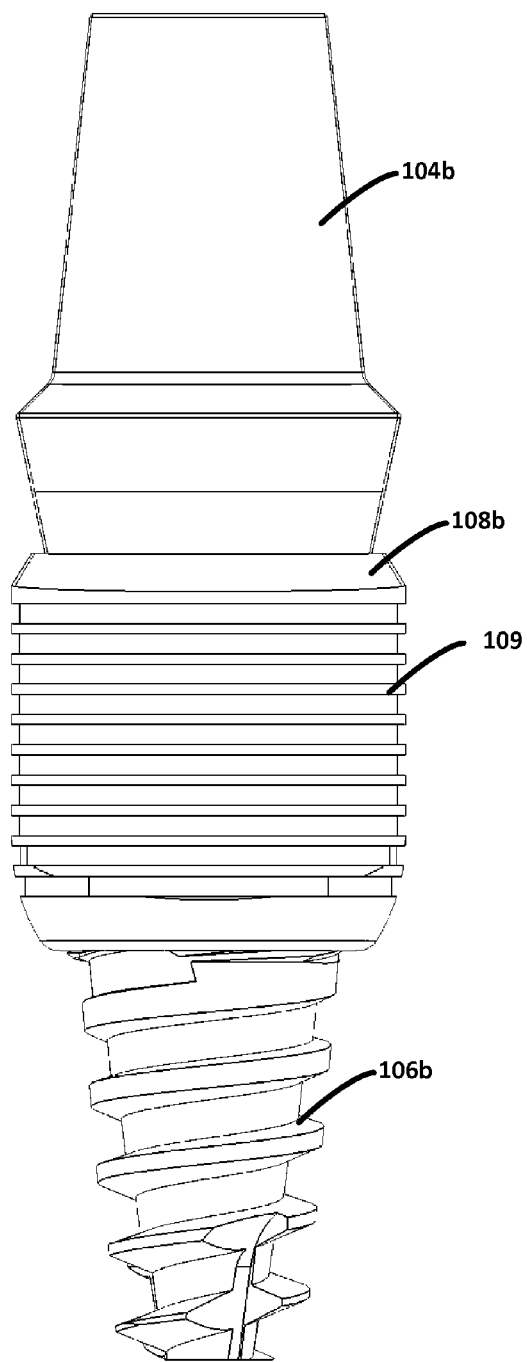
Figure 3A:
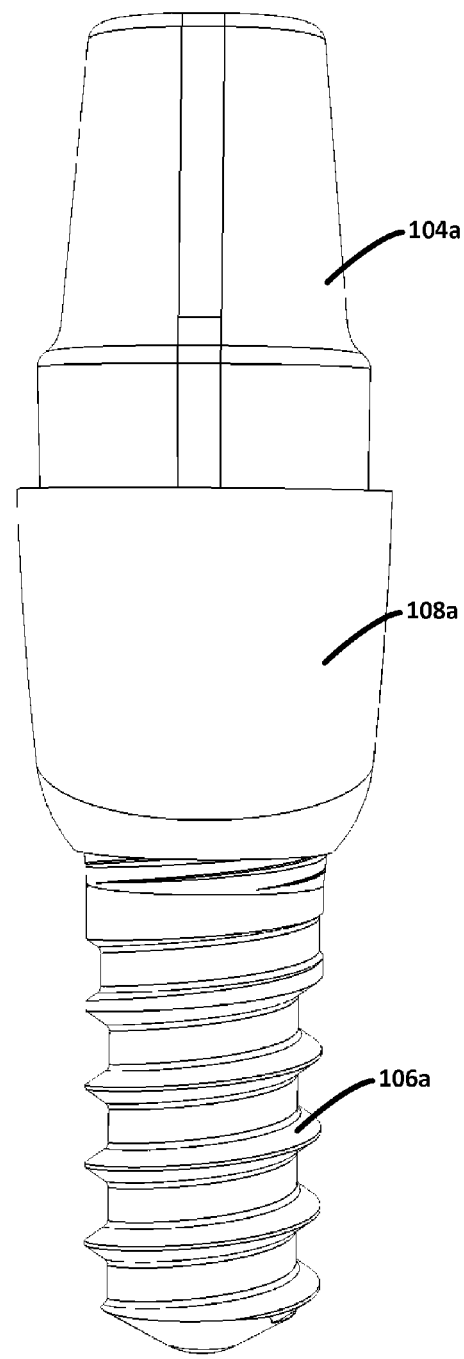
FIGS. 3A-B show another side view of the implant of FIGS. 1A-B.
Figure 3B:
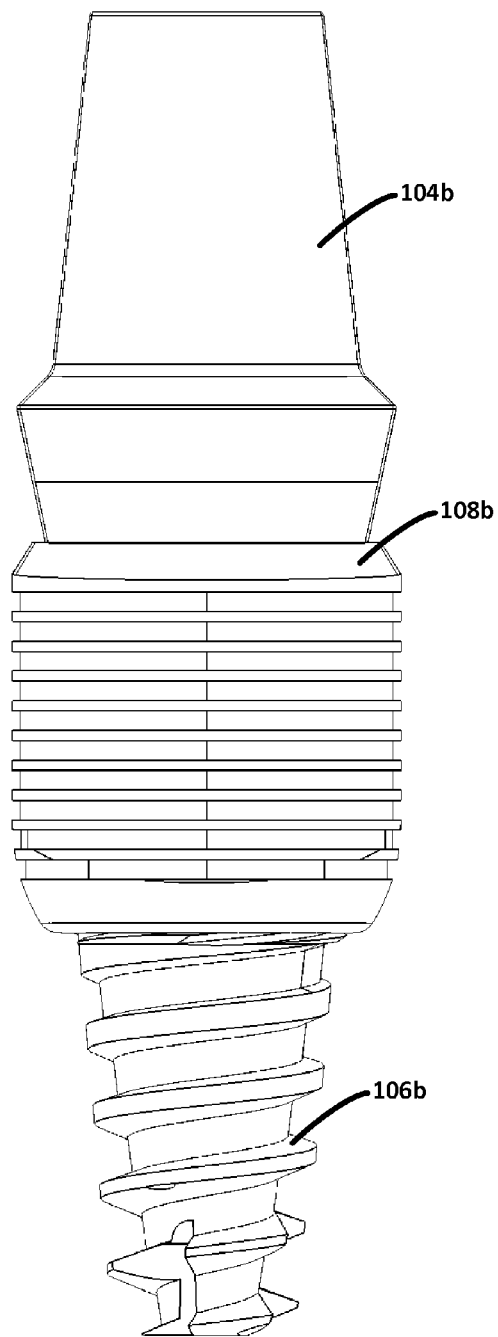
Figure 4A:
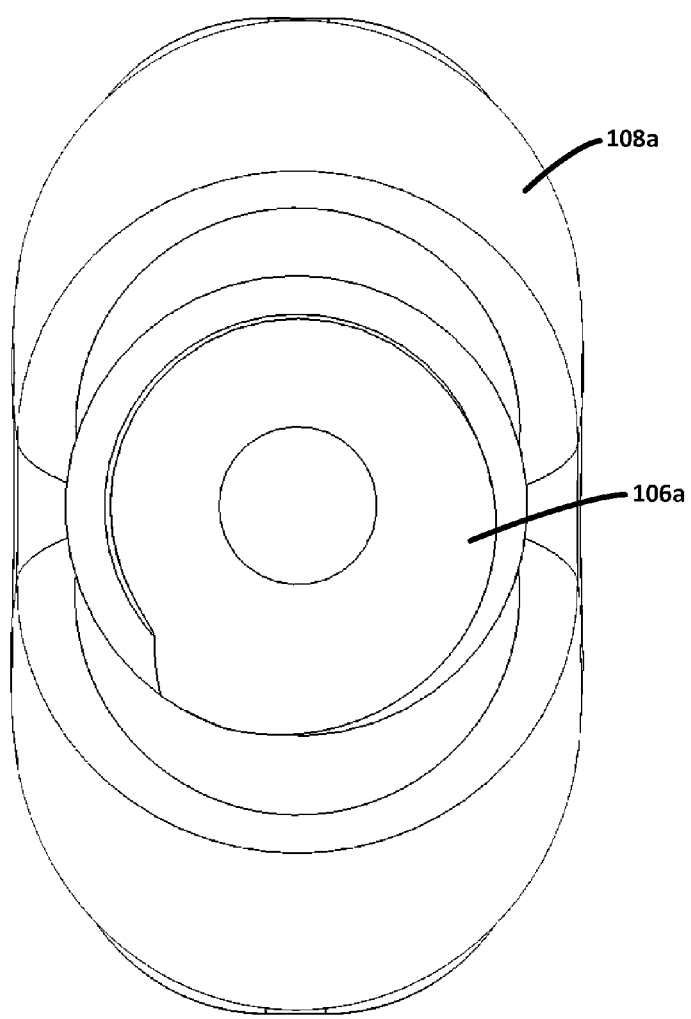
FIGS. 4A-B show a bottom view of the implant of FIGS. 1A-B.
Figure 4B:
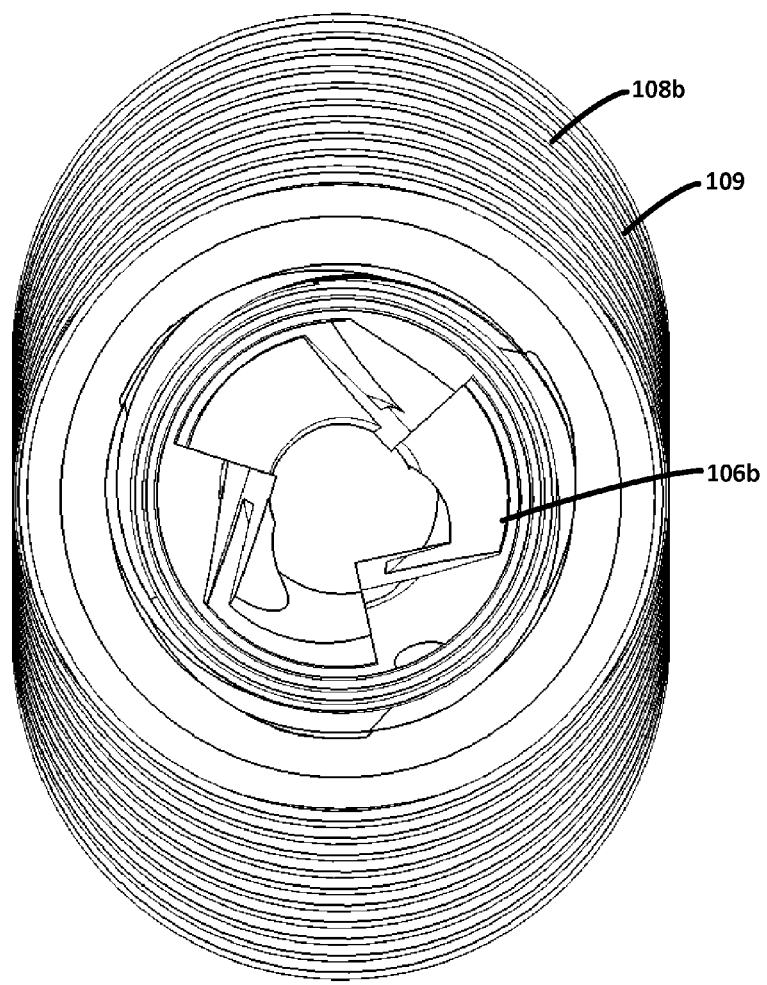
Figure 5A:
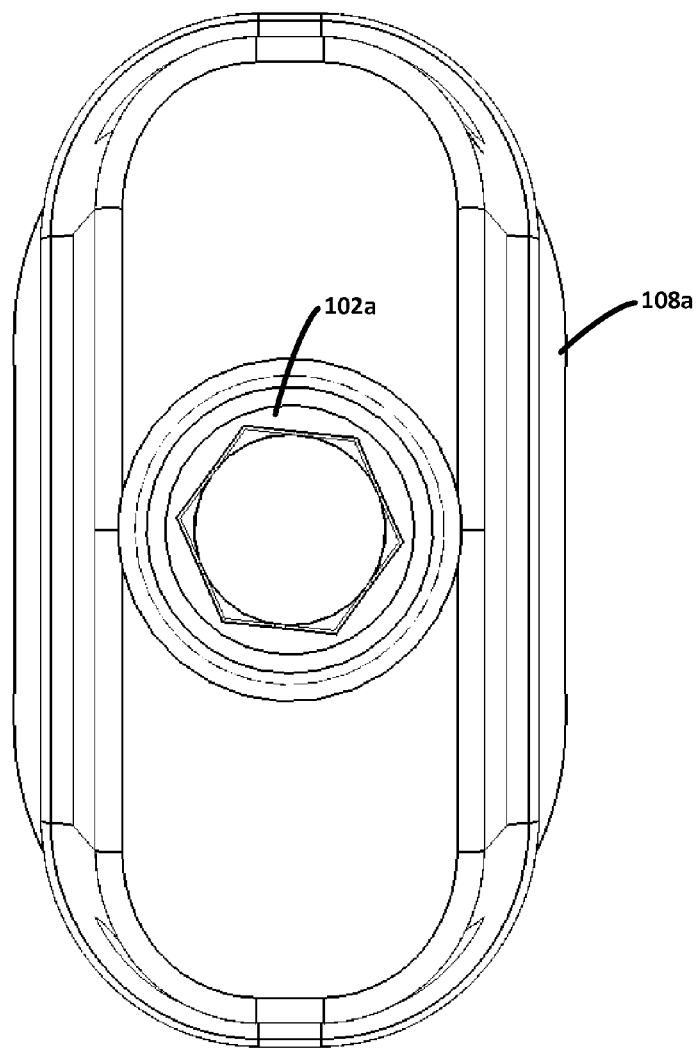
FIGS. 5A-B show a top view of the implant of FIGS. 1A-B.
Figure 5B:
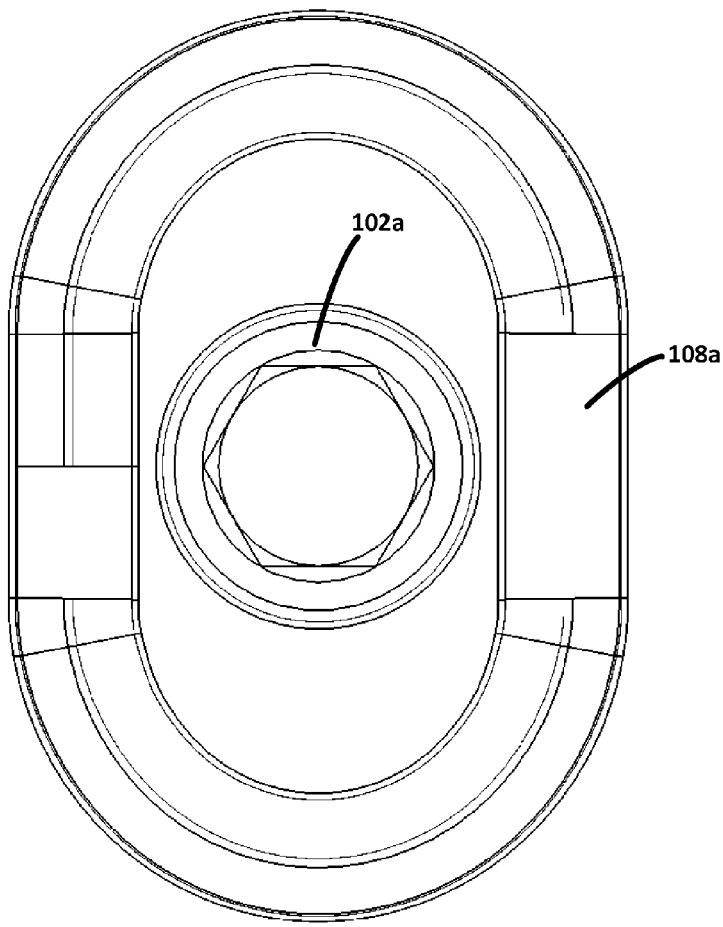
Figure 6A:
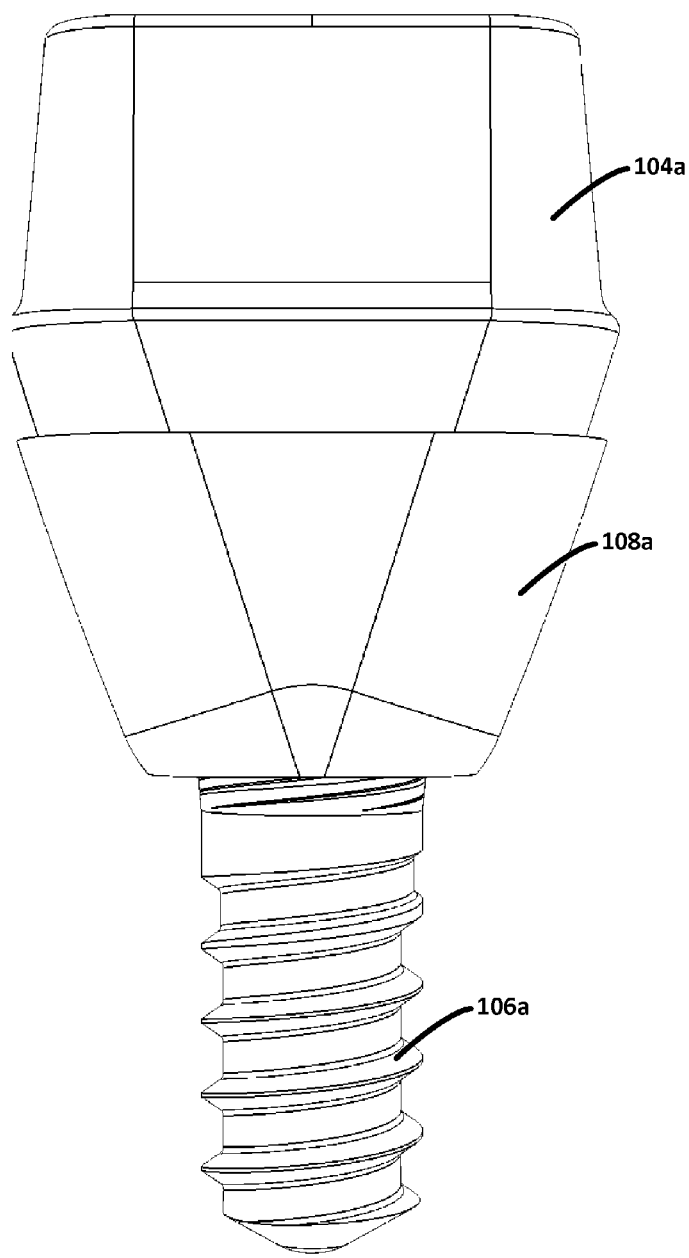
FIGS. 6A-B show another side view of the implant of FIGS. 1A-B.
Figure 6B:
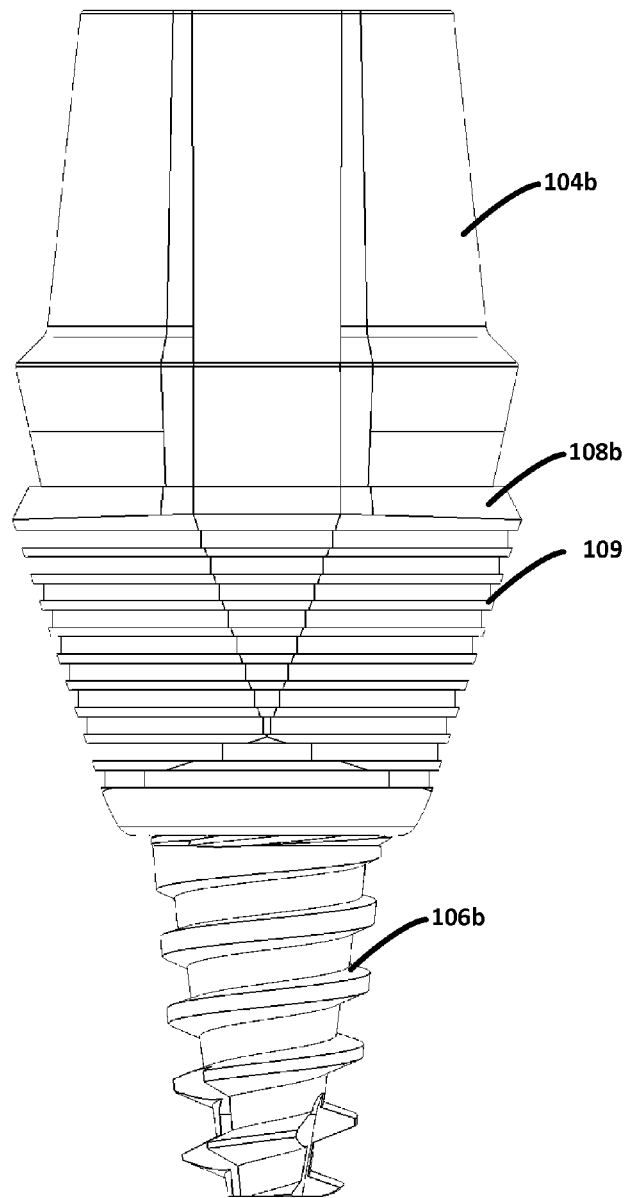
Figure 7A:
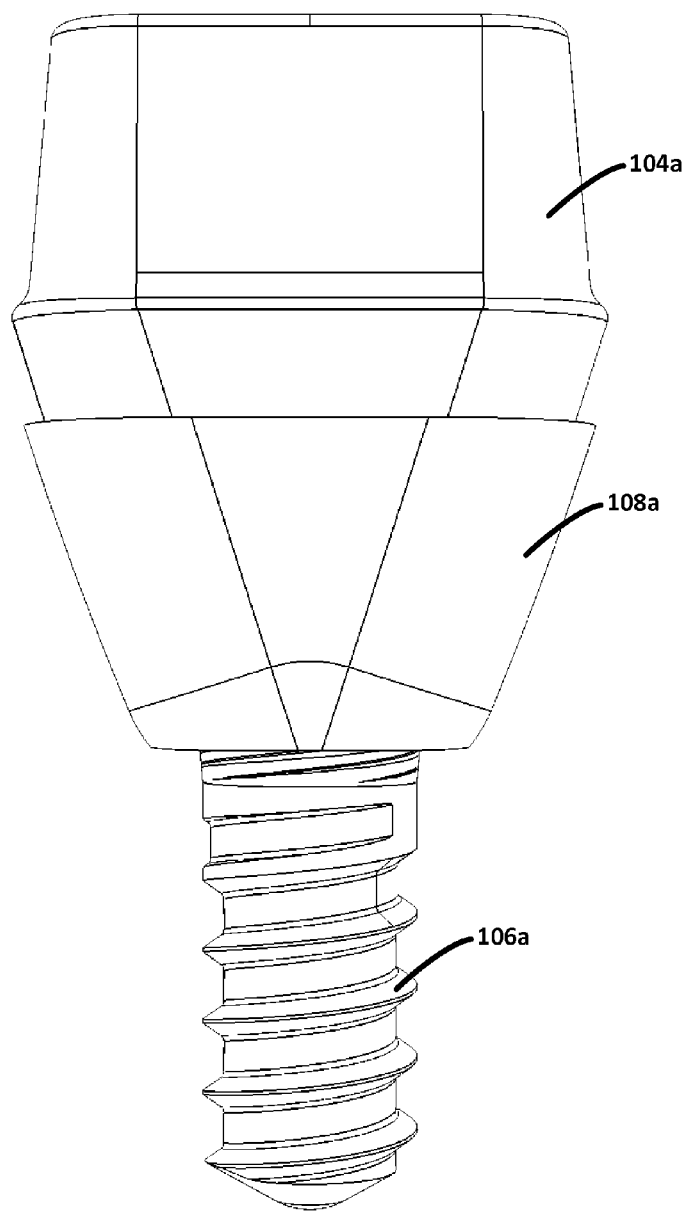
FIGS. 7A-B show another side view of the implant of FIGS. 1A-B.
Figure 7B:
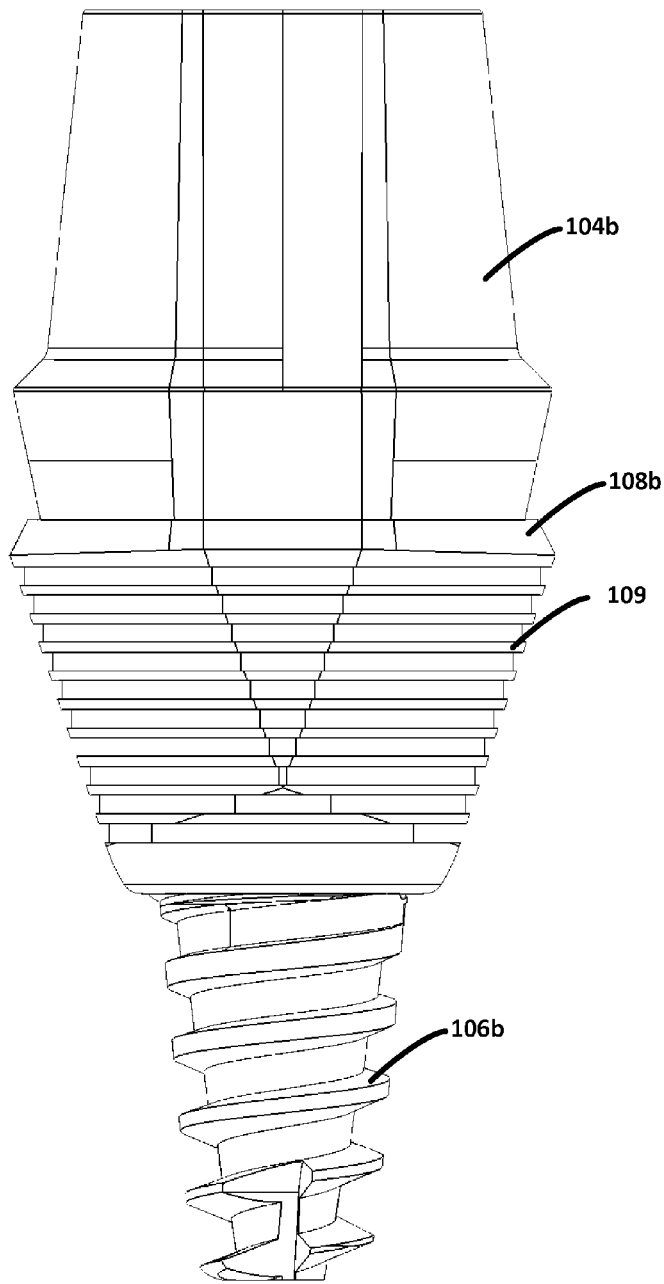

When placing a dental implant as discussed throughout, a space or osteotomy cavity is formed in jawbone and then a base member is positioned into the space. In general, the base member serves as a platform to secure an abutment that in turn receives a dental restoration, such as a crown or denture. In one aspect, the base member is eccentric in cross-section (non-circular and non-radially symmetric) and has a relatively large surface area that is in contact with or integrated into the jawbone, and this decreases stress on the bone, implant, abutment, and crown. In another aspect, the base member has a recess that receives the bottom end of the abutment, which is shaped to match the non-circular and non-radially symmetric geometry of the base member. This provides a precise friction connection for the physician to position the implant within the base in a correct orientation, prevents the abutment from rotating relative to the base member, creates a tight seal, and distributes forces throughout the connected pieces.

Referring now to FIGS. 1A-B through FIGS. 9A-B, and most specifically to FIGS. 8A-B and FIGS. 9A-B, an example dental implant 100(a,b) is shown in accordance with the present disclosure. The dental implant 100 includes or comprises a fastener 102(a,b), an abutment member 104(*a,b*), an implant screw 106(*a,b*), and a base member 108(*a,b*). In practice, the base member 108 is fitted to or positioned within an eccentrically-shaped (e.g., oval-like) osteotomy box or cavity 110 formed within jawbone 112, shown in FIGS. 8A-B in exaggerated and simplified view. Following folding back of tissue 111 and drilling of a pilot hole within the jawbone 112, the implant screw 106 is positioned through a central passage 114(*a,b*), shown FIGS. 22A-B, formed within the base member 108 and then is torqued into place to rigidly secure the base member 108 to the jawbone 112. In some examples, the central passage 114 is tapered and matches a taper in the head of implant screw 106. In so doing, a friction fit or cold weld is formed between the implant screw 106 and the base member 108 similar to that described in U.S. Pat. Nos. 8,562,244 and 8,740,616, incorporated herein by reference.

In some examples, the central passage 114 includes threads that interact or mate with corresponding threads in the head of the implant screw 106 to create a tightly sealed connection whereby the implant screw 106 and surfaces of the central passage 114 are cinched tightly together. More specifically, the threaded connection between the implant screw 106 and the base member 108 serves to maintain the friction fit or cold weld between the tapered sections so as to prevent micro-leakages between the two components. The abutment member 104 may then be fitted to or positioned within the base member 108. The fastener 102 may then be positioned through an internal passage 116(*a,b*), shown FIGS. 22A-B, formed within the abutment member 104 and then may be torqued into place within a receiver 118(*a,b*), also shown FIGS. 22A-B, formed within the implant screw 106, to rigidly secure the abutment member 104 to the base member 108. As may be understood upon inspection of FIGS. 1A-B through FIGS. 9A-B, and in particular FIGS. 8A-B, any particular cross-section A-A of the abutment member 104, and any particular cross-section B-B of the base member 108, is non-circular or eccentric in that an outer surface 103(*a-b*) of the abutment member 104 when viewed in cross-section would exhibit a non-circular or eccentric shape, and similarly an outer surface 105(*a-b*) of the abutment member 104 when viewed in cross-section would exhibit a non-circular or eccentric shape.

Figure 9A:
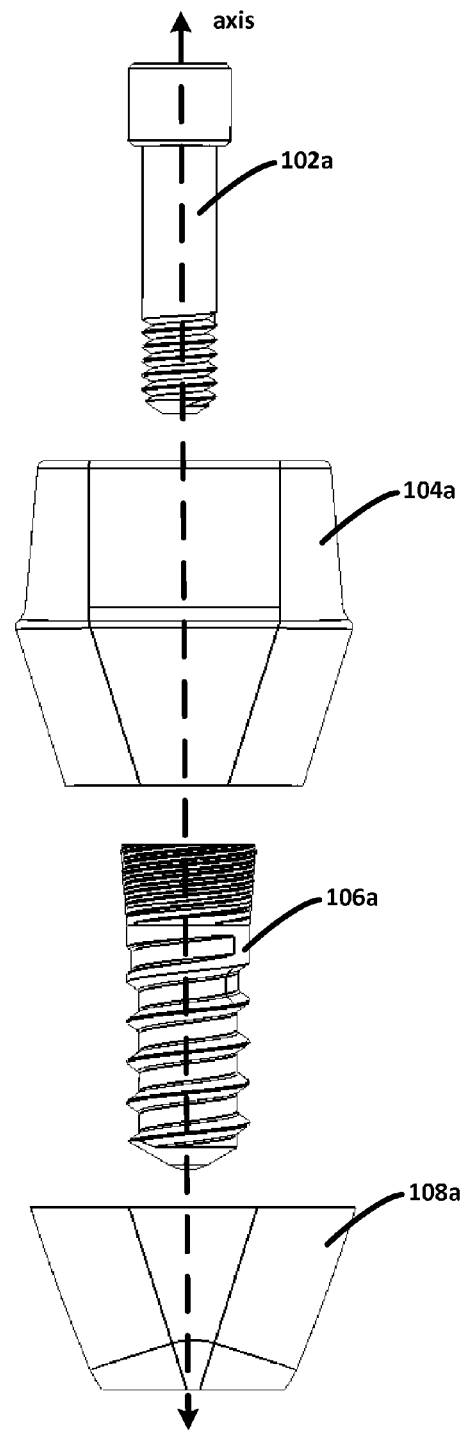
FIGS. 9A-B show an exploded view of the implant of FIGS. 1A-B.
Figure 9B:
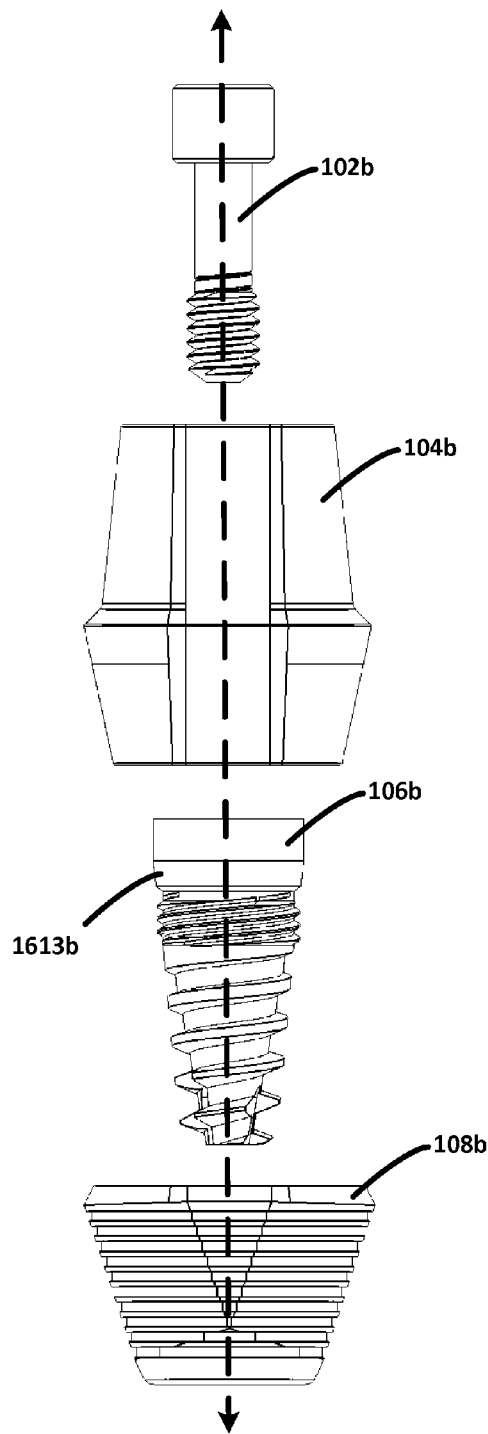
Figure 10A:
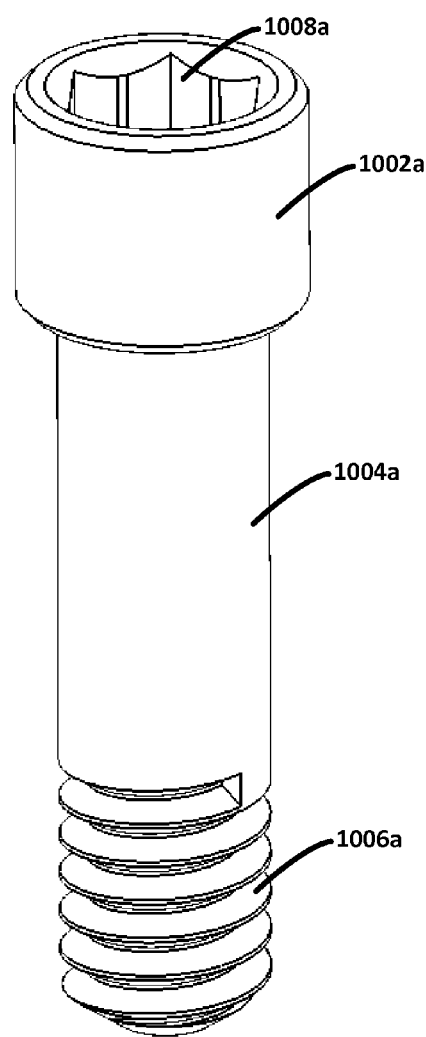
FIGS. 10A-B show a first screw of the implant of FIGS. 1A-B.
Figure 10B:
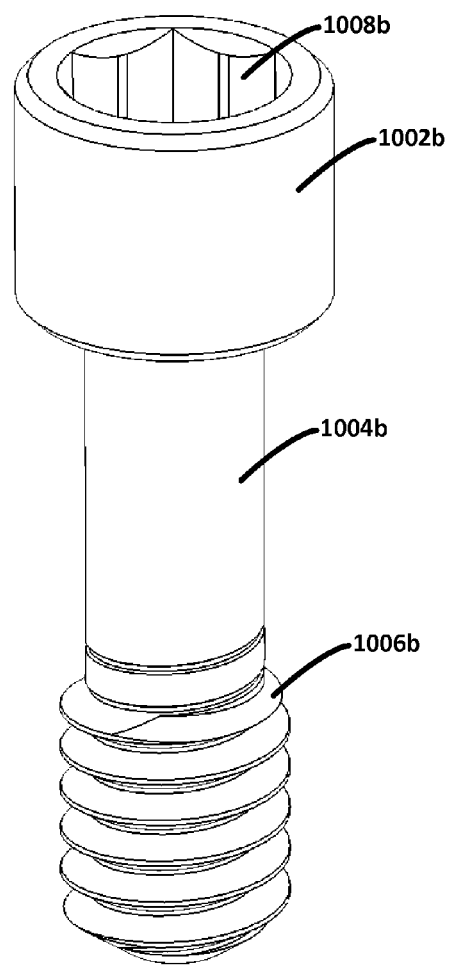
Figure 11A:
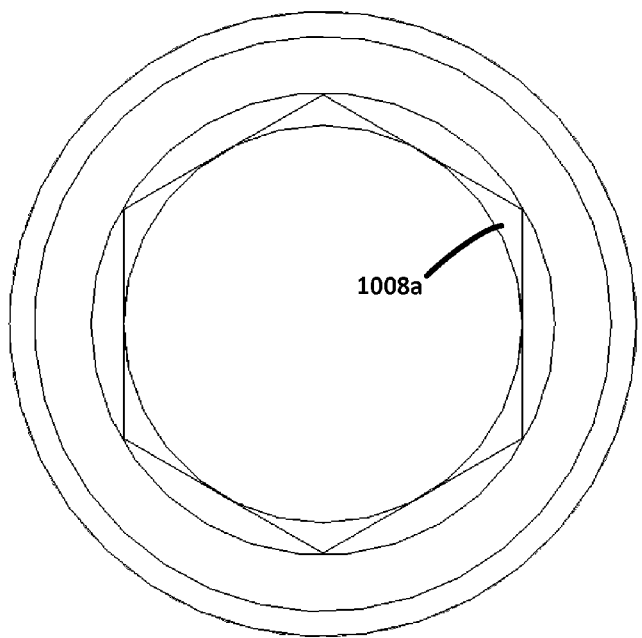
FIGS. 11A-B show a top view of the screw of FIGS. 10A-B.
Figure 11B:
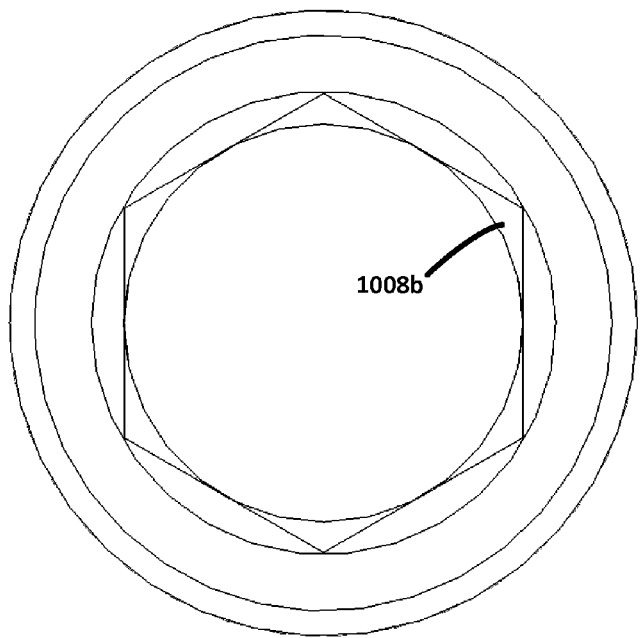
Figure 12A:
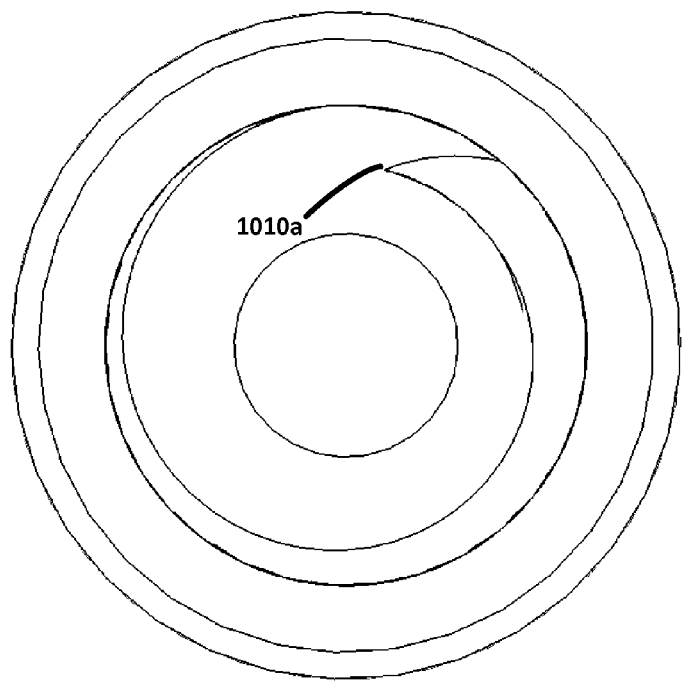
FIGS. 12A-B show a bottom view of the screw of FIGS. 10A-B.
Figure 12B:
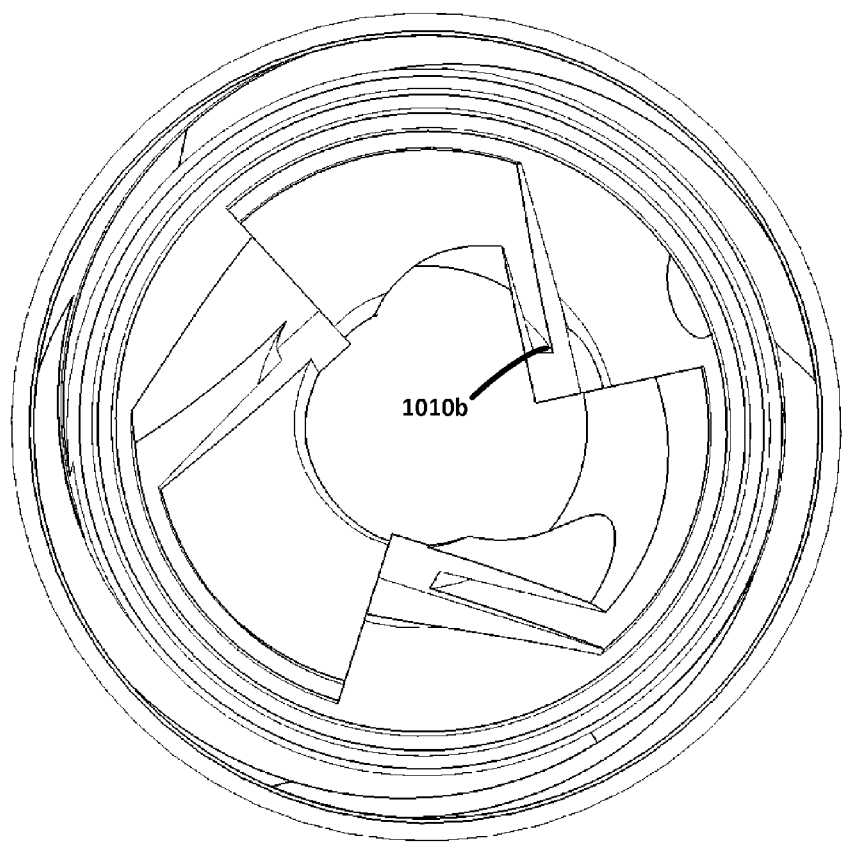
Figure 13A:
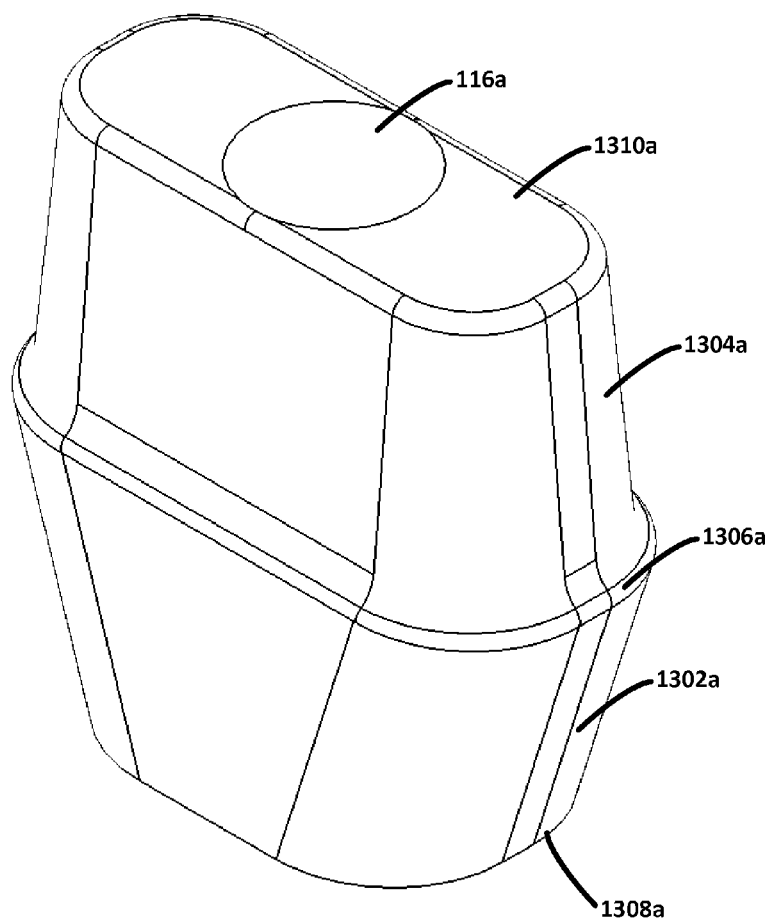
FIGS. 13A-B show an abutment of the implant of FIGS. 1A-B.
Figure 13B:
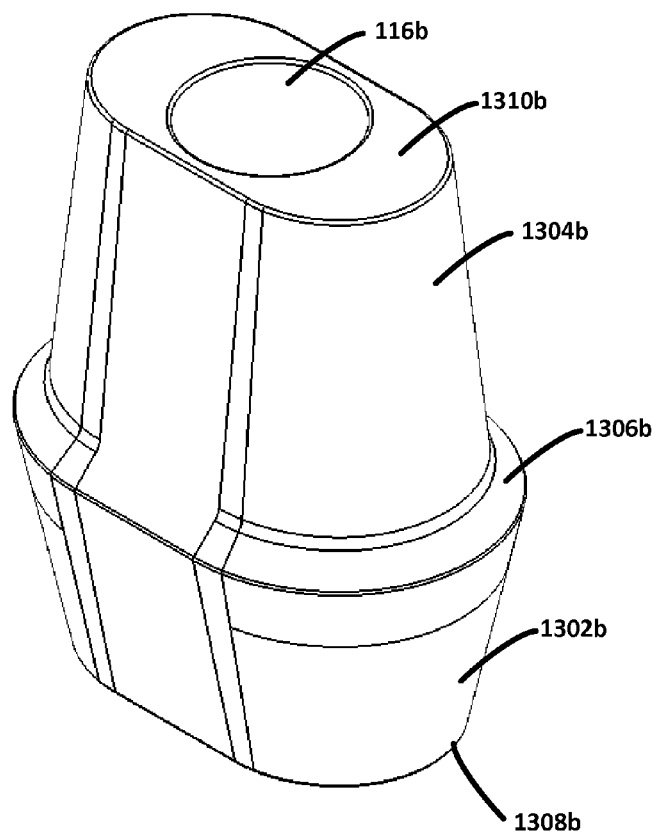

Referring now to FIGS. 10A-B through FIGS. 12A-B, multiple views of the fastener 102 are shown in accordance with the present disclosure. In this example, the fastener 102 includes a head portion 1002(*a,b*), a shank portion 1004(*a,b*), and a thread portion 1006(*a,b*). The head portion 1002 is an extension of the shank portion 1004, and includes a keyed-aperture 1008(*a,b*) that provides a bearing surface(s) for a tip or bit of a torque-applying tool (not shown). The thread portion 1006 is formed within the shank portion 1004 and includes at least one leading edge 1010(*a,b*), shown in FIGS. 12A-B. In comparison, the thread portion 1006*a* has an OD (Outer Diameter) that substantially or approximately matches an OD of the shank portion 1004*a*, whereby the thread portion 1006*b* has an OD that is greater than an OD of the shank portion 1004*b*. Additionally, the thread portion 1006 may be tapered so that an OD of the thread portion 1006 near the leading edge 1010 is less than an OD of the thread portion 1006 at an end of the thread portion 1006 opposite the leading edge 1010. The OD of the thread portion 1006 may be measured with respect to a longitudinal axis of the fastener 102 and the dental implant 100 as shown in FIGS. 9A-B. In some examples, the fastener 102 may be formed of zirconia or titanium material. Other examples are possible.

Figure 14A:
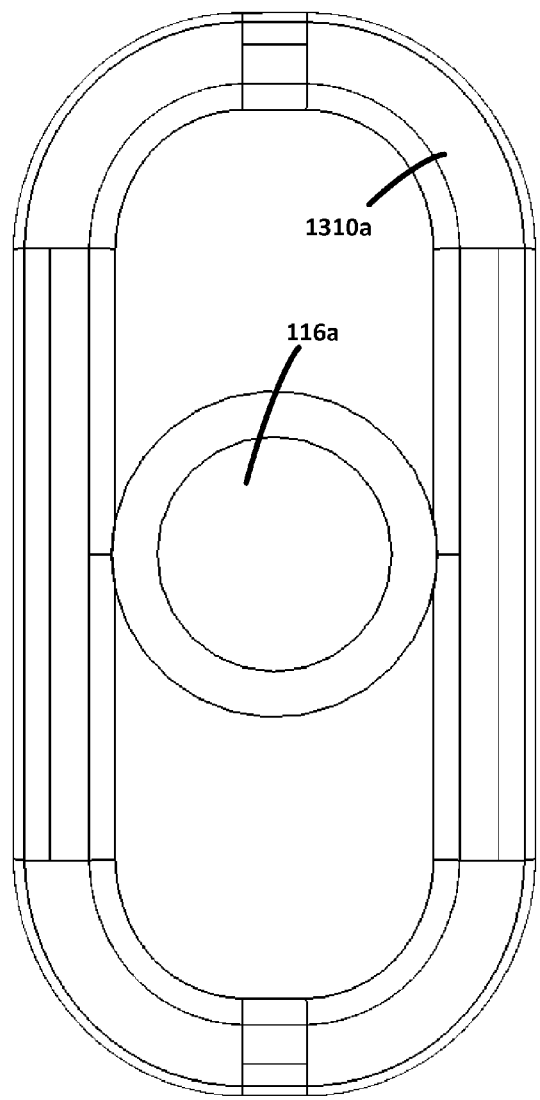
FIGS. 14A-B show a top view of the abutment of FIGS. 13A-B.
Figure 14B:
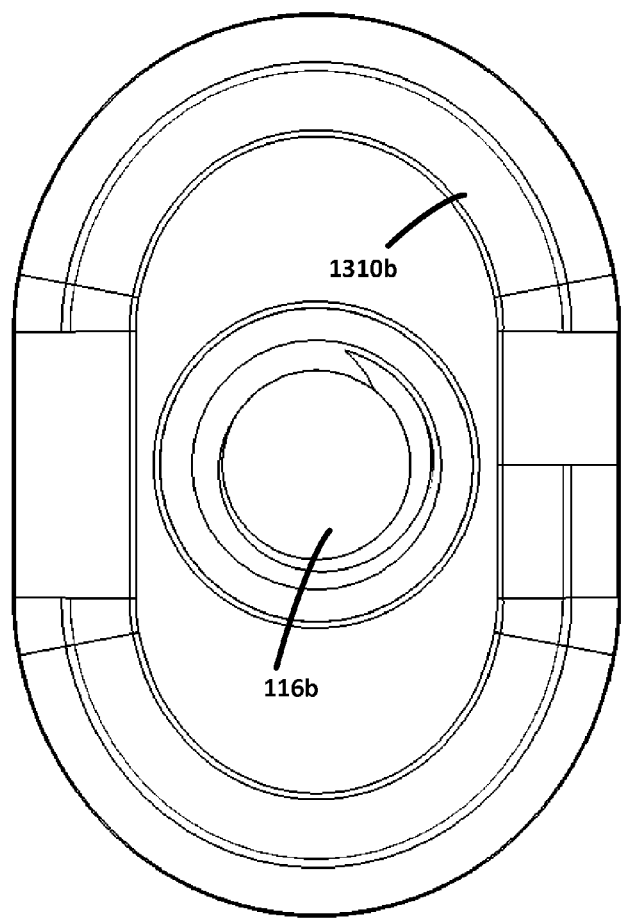
Figure 15A:
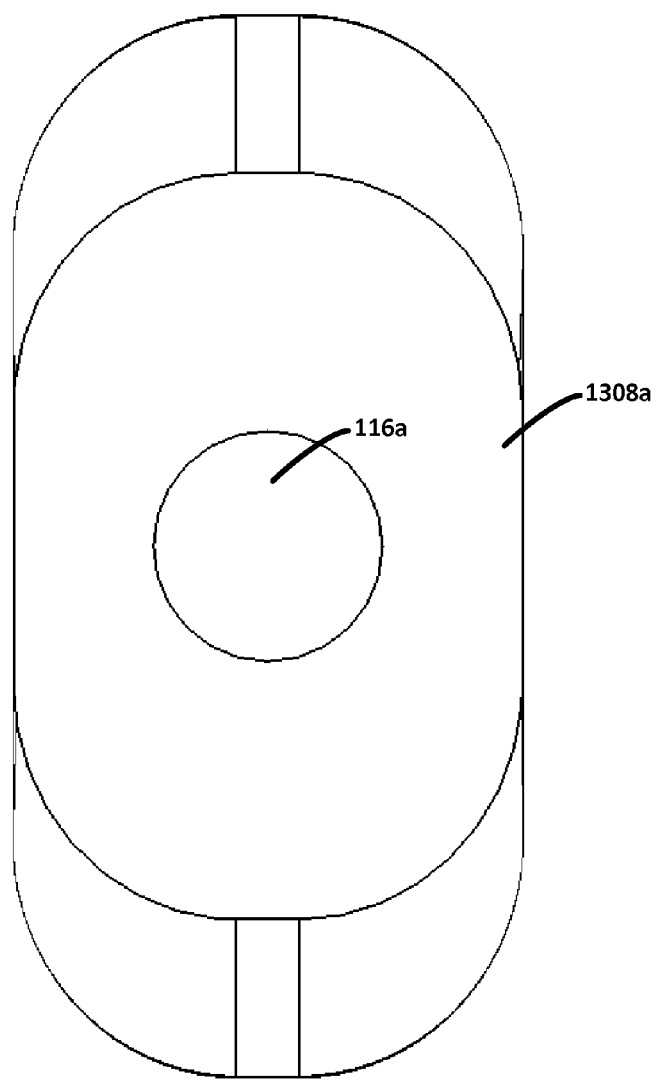
FIGS. 15A-B show a bottom view of the abutment of FIGS. 13A-B.
Figure 15B:
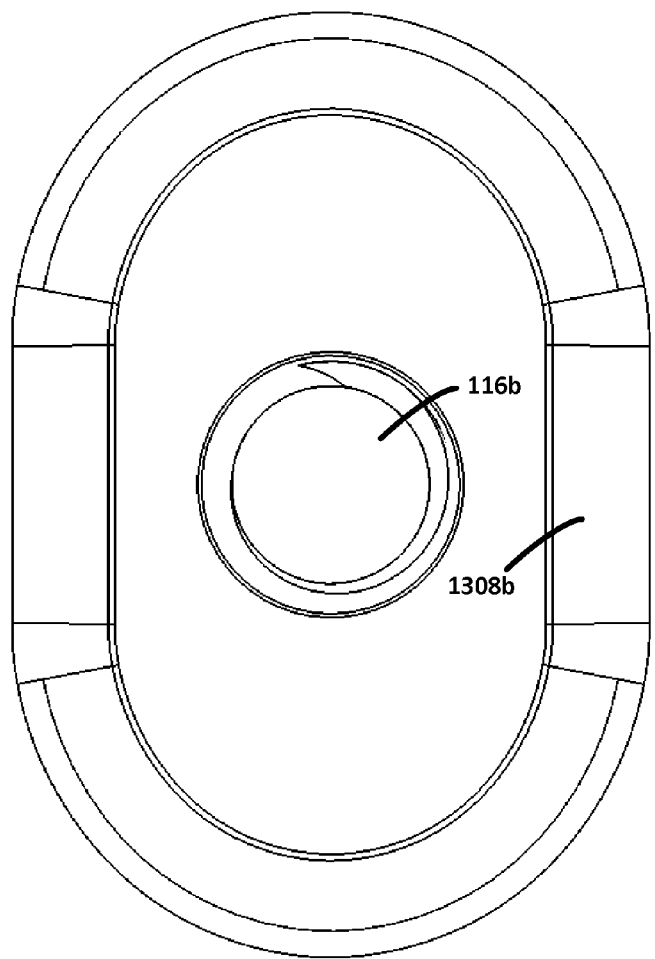

Referring now to FIGS. 13A-B through FIGS. 15A-B, multiple views of the abutment member 104 are shown in accordance with the present disclosure. In this example, and as mentioned above, an internal passage 116 is formed within the abutment member 104. The internal passage 116 is shaped so that the fastener 102 may be positioned thereto, and then torqued into place within the receiver 118 that is formed within the implant screw 106. The abutment member 104 further exhibits external features including a first portion 1302(*a,b*) and a second portion 1304(*a,b*) separated by a flared ridge 1306(*a,b*). The first portion 1302 tapers inwardly as measured with respect to a longitudinal axis of the abutment member 104 and the dental implant 100 as shown in FIGS. 9A-B, starting from the ridge 1306 moving towards an end 1308(*a,b*) of the first portion 1302 opposite the ridge 1306. Similarly, the second portion 1304 tapers inwardly as measured with respect to the longitudinal axis of the abutment member 104, starting from the ridge 1306 moving towards an end 1310(*a,b*) of the second portion 1304 opposite the ridge 1306. FIGS. 14A-B and FIGS. 15-B show the non-circular, oblong, or oval shape of the ends 1308, 1310 of the example abutment member 104. In general, the shape of the ends 1308, 1310 may be defined so as to match the shape of portions of the base member 108, to prevent rotation of the abutment member 104 when positioned to the base member 108, and also provide a mechanism to easily lock the abutment member 104 in place. Other shapes of the abutment member 104 (and base member 108) are possible.

For example, the ends 1308, 1310 of the abutment member 104 may exhibit any polygonal shape as desired, or other irregular shapes such as a double-lobe or "FIG. 8" and/or a lemniscate shape. Other examples are possible. For example, it is contemplated that one or more features or elements of the abutment member 104, base member 108, etc., may be formed to exhibit a non-round asymmetrical shape. Further, in some examples, the abutment member 104 may be formed of a white zirconia material to more closely match crown coloring. In some examples, dimensions of the abutment member 104 may be in a range from about 5.0 millimeters to about 12.0 millimeters inclusive in total height, and various combinations of dimensions at the rim ranging from about 4.0 millimeters to about 10.0 millimeters inclusive.

Figure 18A:
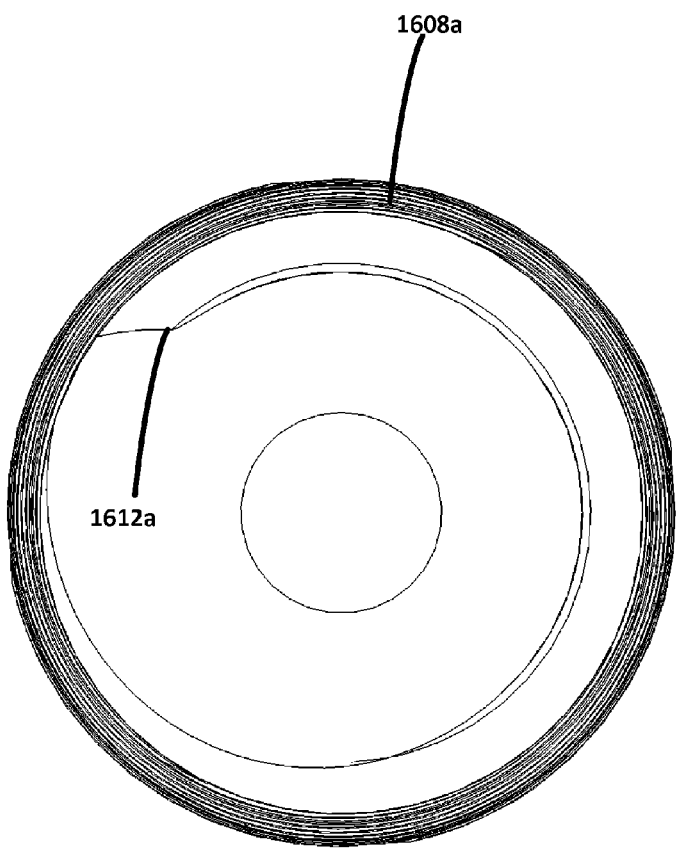
FIGS. 18A-B show a bottom view of the screw of FIGS. 16A-B.
Figure 18B:
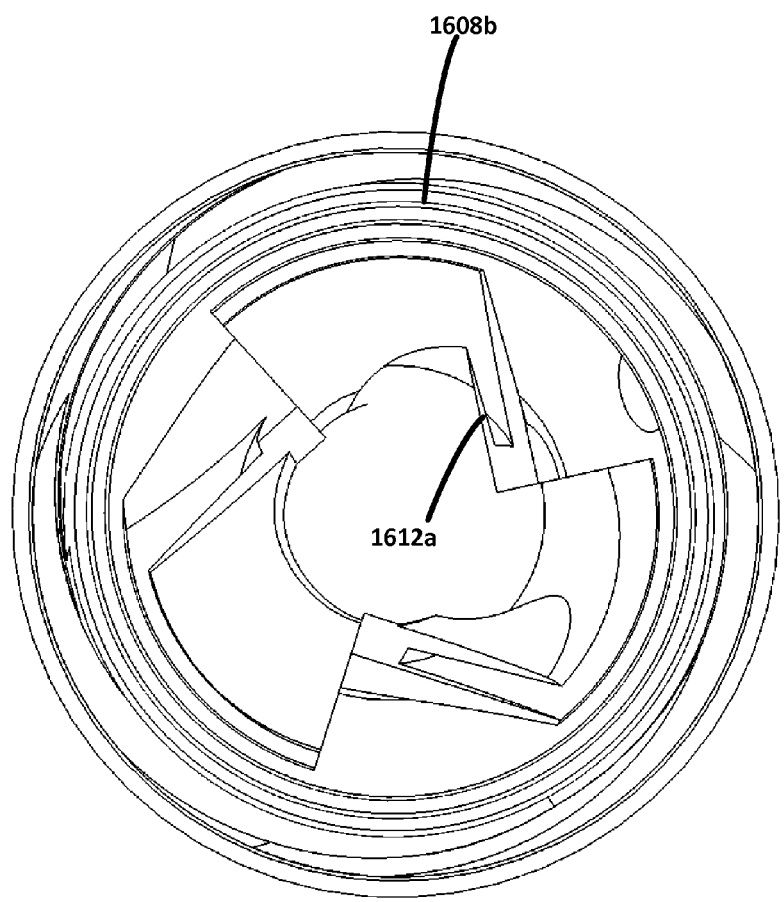
Figure 22A:
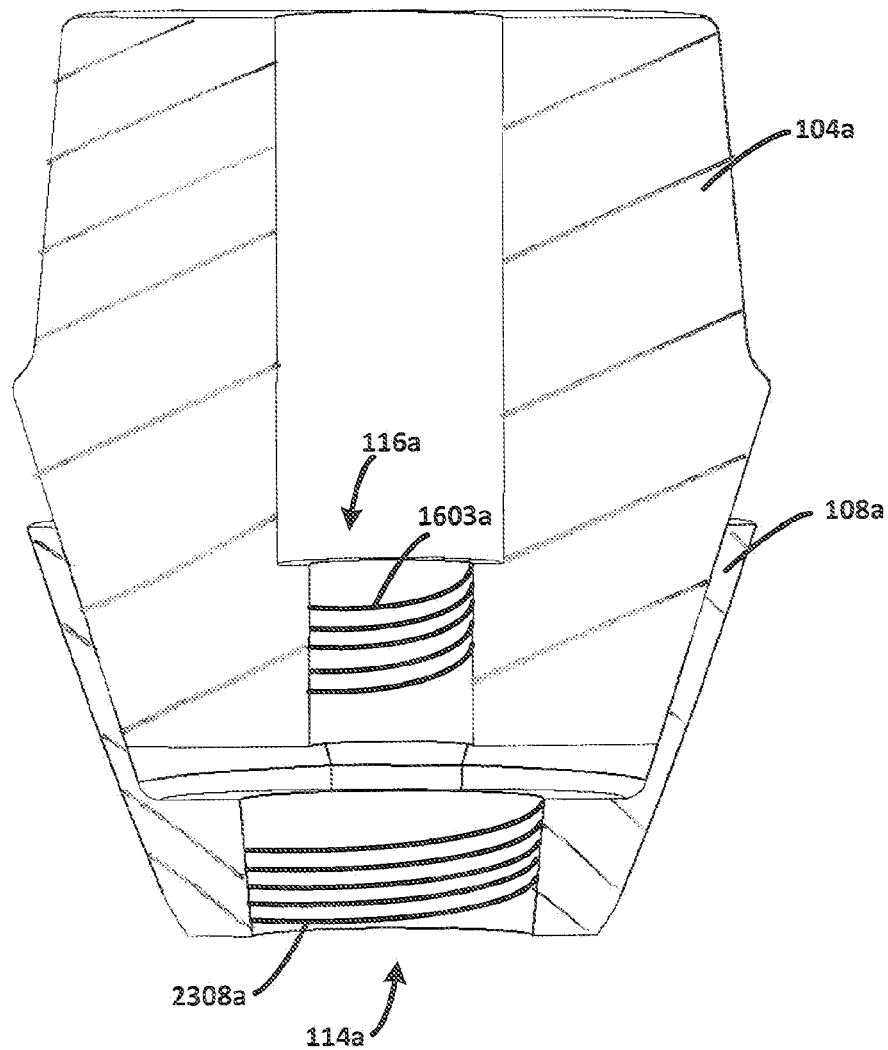
FIGS. 22A-B show certain components of FIGS. 8A-B.
Figure 22B:
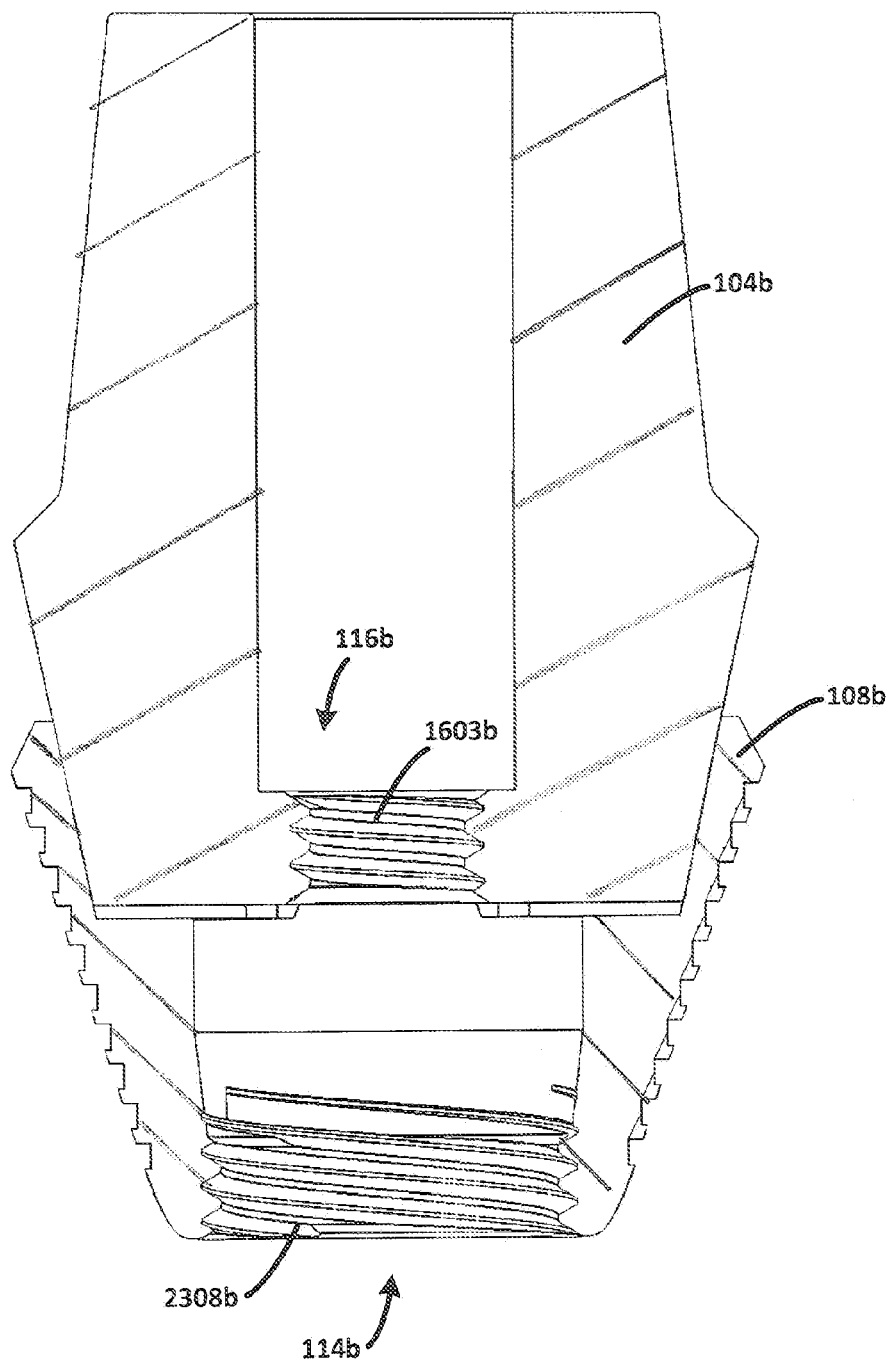

Referring now to FIGS. 16A-B through FIGS. 18A-B, multiple views of the implant screw 106 are shown in accordance with the present disclosure. In this example, and as mentioned above, a receiver 118 is formed within the implant screw 106. Referring additionally to FIGS. 23A-D, the receiver 118 is shaped to include a female thread 1602(*a,b*) so that the thread portion 1006 of the fastener 102 may be threaded thereto. Referring additionally to FIGS. 22A-B, the internal passage 116 formed within the abutment member 104 is shaped to include a female thread 1603(*a,b*) so that the thread portion 1006 of the fastener 102 may be positioned and threaded thereto. Additionally, the implant screw 106 exhibits a number of features similar to the fastener 102. For example, the implant screw 106 includes a head portion 1604(*a,b*), a shank portion 1606(*a,b*), and a thread portion 1608(*a,b*). The head portion 1604 is an extension of the shank portion 1606, and includes a keyed-aperture 1610(*a,b*) that provides a bearing surface(s) for a tip or bit of a torque-applying tool. Further, the thread portion 1608 is formed within the shank portion 1606 and includes at least one leading edge 1612 as shown in FIGS. 18A-B. The head portion 1604 of the implant screw 106 though includes an external feature different than the head portion 1002 of the implant screw 106.

Figure 16A:
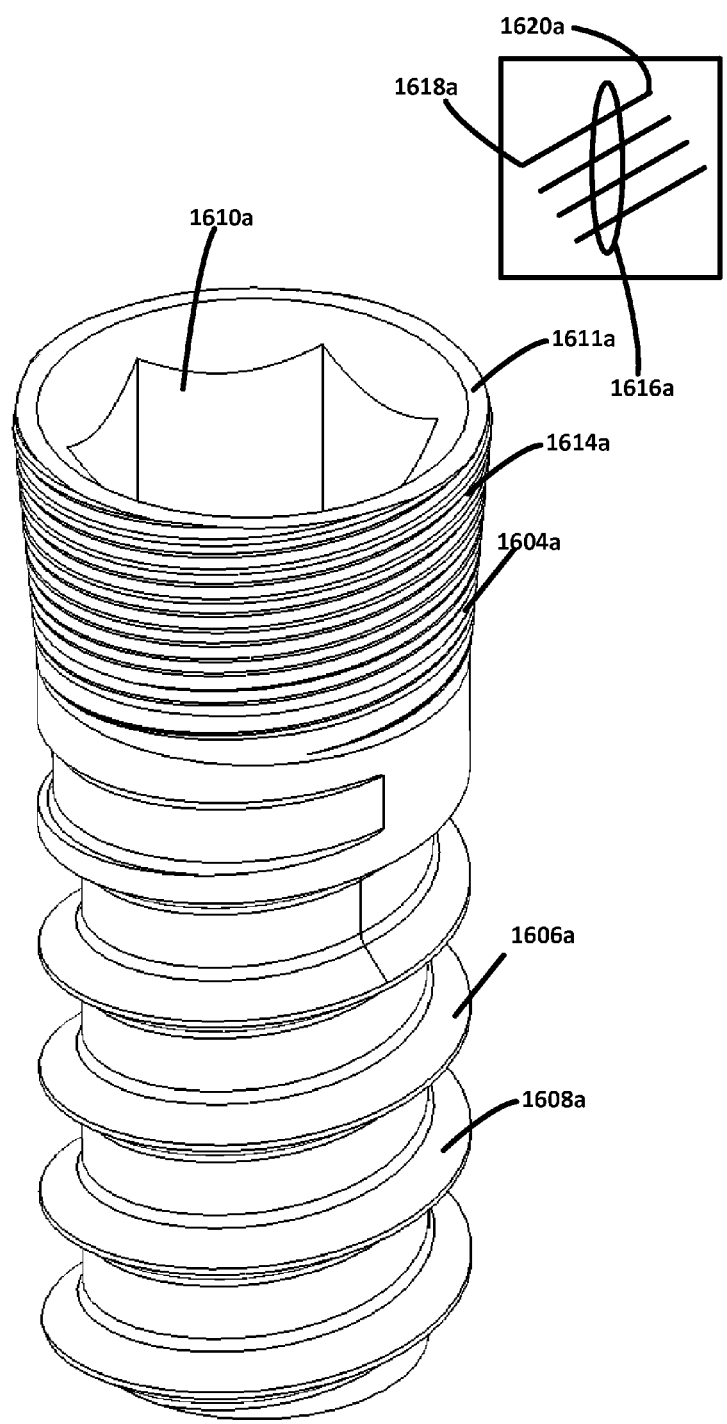
FIGS. 16A-B show another screw of the implant of FIGS. 1A-B.
Figure 16B:
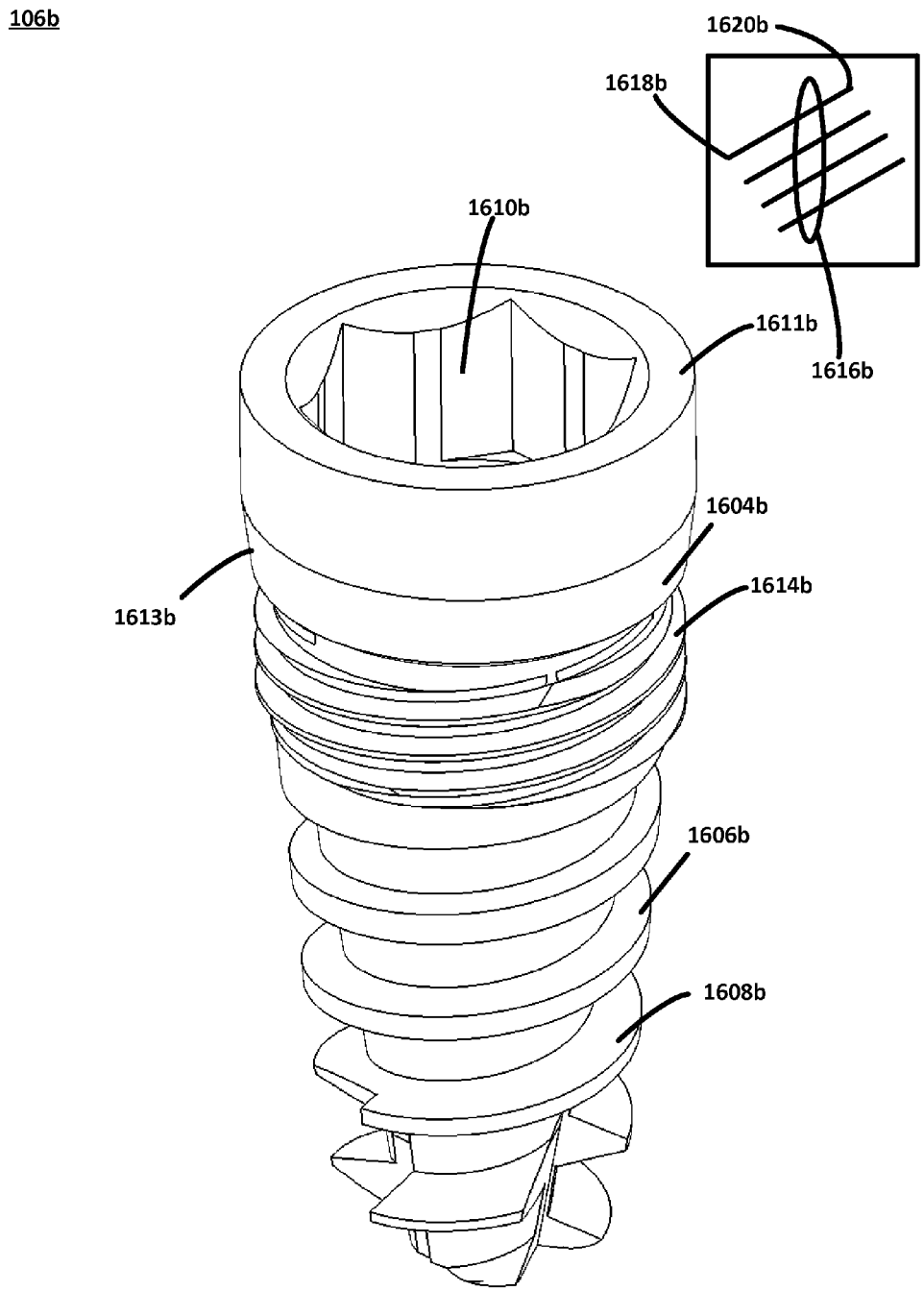
Figure 17A:
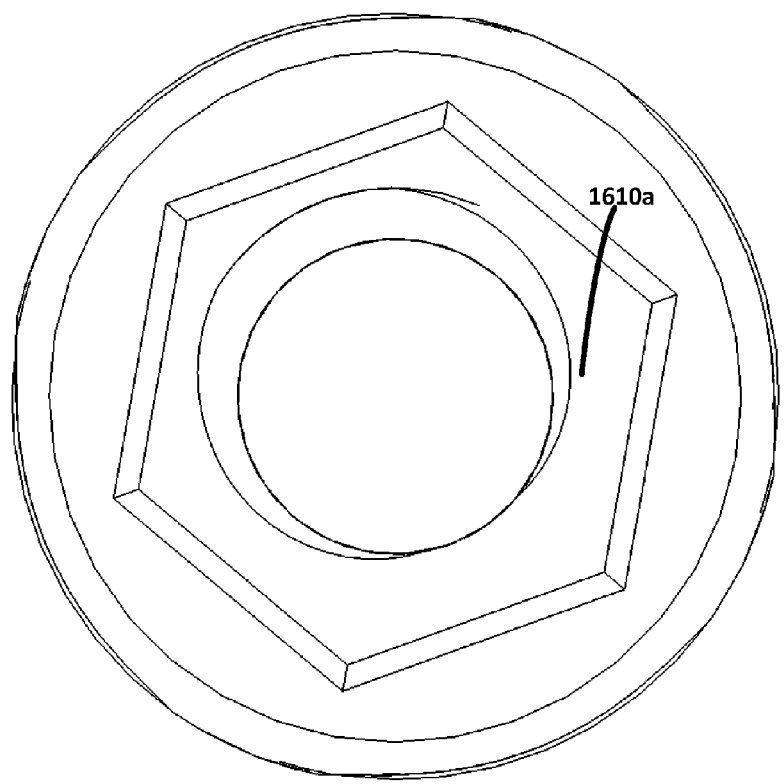
FIGS. 17A-B show a top view of the screw of FIGS. 16A-B.
Figure 17B:
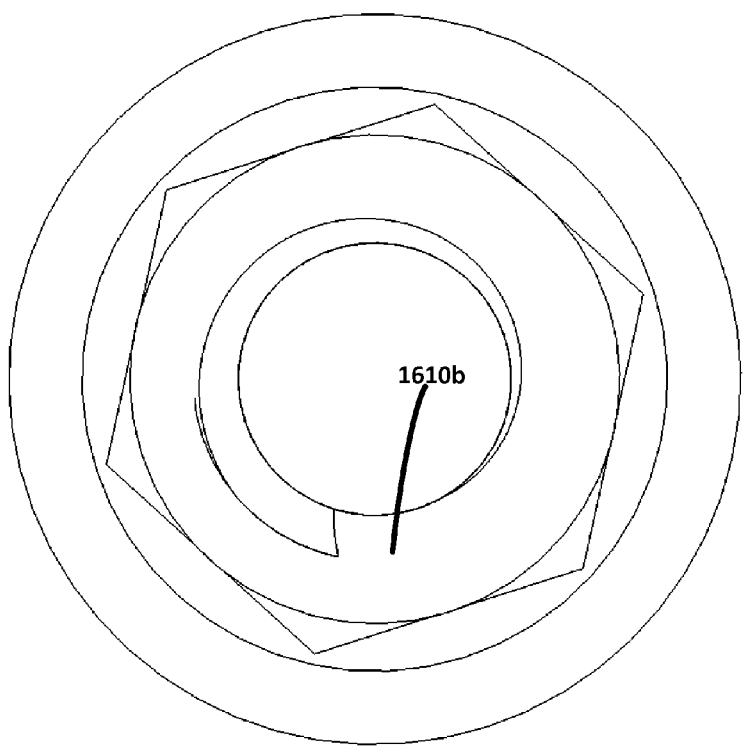

In particular, the head portion 1604 includes an external thread 1614(a,b), whereby each level or full turn of the external thread 1614 includes multiple open leads. This is illustrated in FIGS. 16A-B where the head portion 1604 is projected onto a plane to show a number of individual threads 1616(a,b) of the external thread 1614, whereby each one of the individual threads 1616 includes a first end or open lead 1618(a,b) and terminates in a second end or open lead 1620(a,b). In general, this is an optional feature, where the head portion 1604 does not necessarily have to include the external thread 1614, but when does so the external thread 1614 in general may exhibit a pitch different than thread portion 1608. Additionally, it is contemplated that the external thread 1614 may be formed at any position along a length of the implant screw 106. For example, the external thread 1614a is shown immediately adjacent to a top edge 1611a of the implant screw 106 in FIG. 16A, whereas the external thread 1614b is shown offset from a top edge 1611b of the implant screw 106 in FIG. 16B. Advantageously, the implant screw 106 in FIG. 16B may be easier to manufacture since the external thread 1614b is not formed on a tapered portion of the implant screw 106. See also FIG. 9B. In comparison, the implant screw 106 in FIG. 16A may be more difficult to manufacture since the external thread 1614a is formed on a tapered portion of the implant screw 106. See also FIG. 9A.

Additionally, the external thread 1614 may not necessarily be formed of multiple open leads, and instead may be formed of a single thread with only first and second open ends. Additionally, the head portion 1604 of the implant screw 106 may taper inwardly as measured with respect to a longitudinal axis of the implant screw 106 as shown in FIGS. 9A-B, starting from an end associated with the keyed aperture 1610 moving towards the thread portion 1608. As discussed further below, the base member 108 includes features that are complementary to the external features of the head portion 1604. In some examples, the implant screw 106 may be formed of a titanium or zirconia material. In some examples, dimensions of the implant screw 106 may be in a range from about 3.0 millimeters to about 5.0 millimeters in diameter inclusive, and in a range from about 8.0 millimeters to about 16.0 millimeters in length inclusive. In some examples, a taper angle of the head portion 1604 may be in a range from about 1.0 degrees to about 15.0 degrees inclusive.

Referring now to FIGS. 19A-B through FIGS. 21A-B, multiple views of the implant screw 106 are shown in accordance with the present disclosure. In this example, and as mentioned above, a central passage 114 is formed within the base member 108. The central passage 114 is shaped so that the implant screw 106 may be positioned thereto, and then torqued into place to rigidly secure the base member 108 to the jawbone 112. Other examples are possible. For instance, in some examples the central passage 114 is not formed within the base member 108. In this example, the base member 108 may be formed of a relatively soft tappable resin material where during implant the implant screw 106 may "tap" the base member 108 to form the central passage 114 at various angles in situ.

The base member 108 further exhibits features complementary to the abutment member 104. For example, referring now additionally to FIGS. 22A-B which shows only the abutment member 104 positioned to the base member 108, the base member 108 includes a 1902(a,b) that is adjacent to the central passage 114. The receiver 1902 is defined by a tapered inner surface 1904(a,b) that is complementary to the tapered first portion 1302 of the abutment member 104. When the first portion 1302 of the abutment member 104 is positioned to the receiver 1902 of the base member 108, and the fastener 102 is positioned through the internal passage 116 formed within the abutment member 104 and torqued into place within the receiver 118 of the implant screw 106, the abutment member 104 is rigidly secured to the base member 108. Such an implementation or fitting may advantageously make it easy for a physician to slip the abutment member 104 into the base member 108 with a correct or proper orientation, and also prevent the abutment member 104 from rotating with respect to the base member 108 due to the complementary oblong or oval geometry of these pieces. Other shapes of the base member 108 are possible.

Figure 19A:
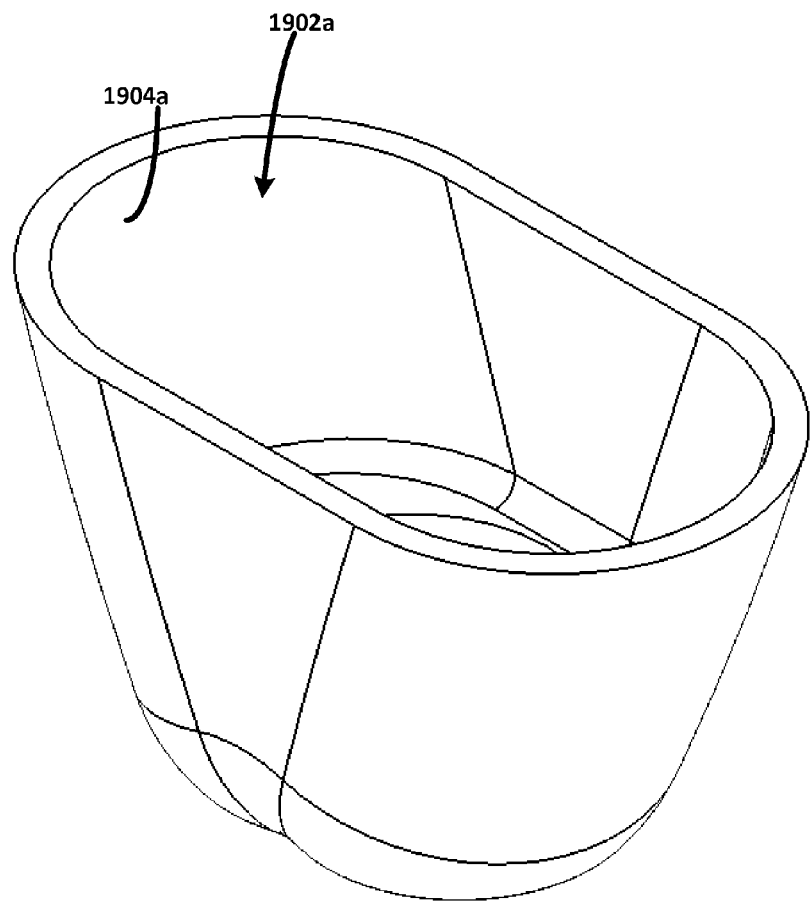
FIGS. 19A-B show a base of the implant of FIGS. 1A-B.
Figure 19B:
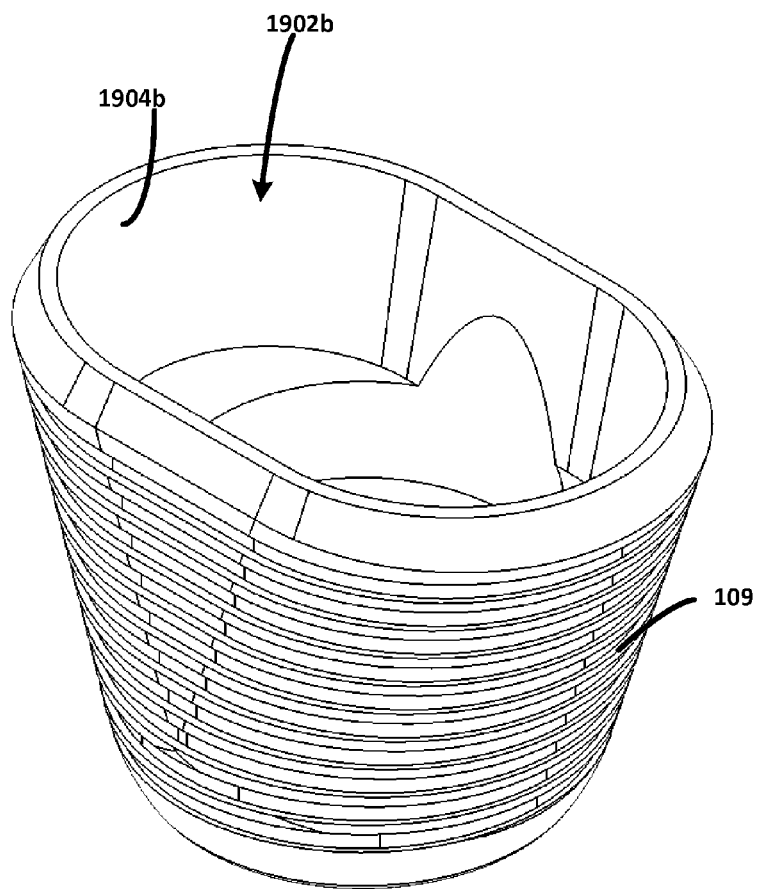
Figure 20A:
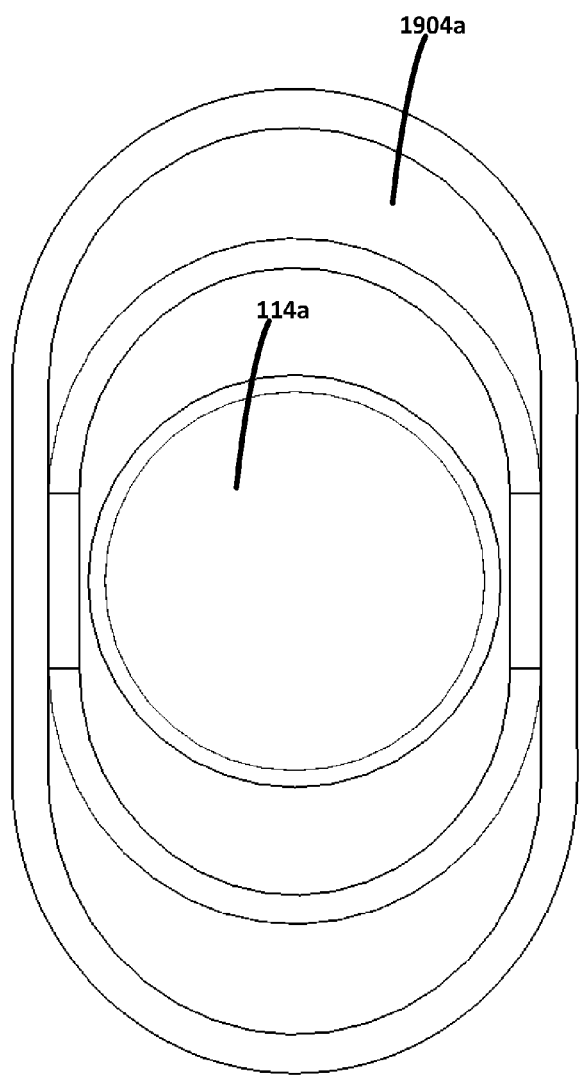
FIGS. 20A-B show a top view of the base of FIGS. 19A-B.
Figure 20B:
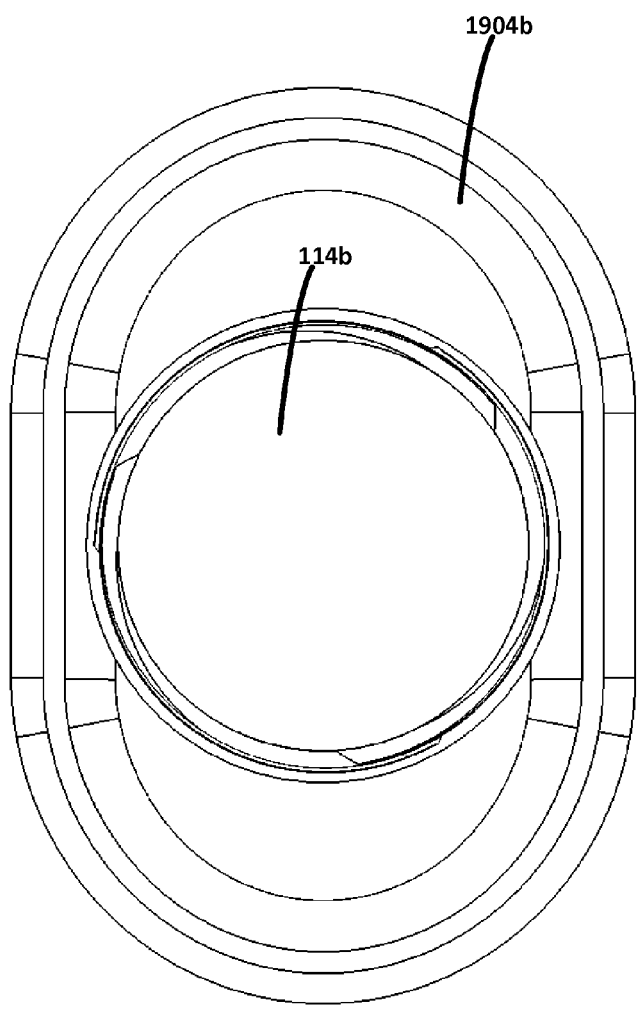
Figure 21A:
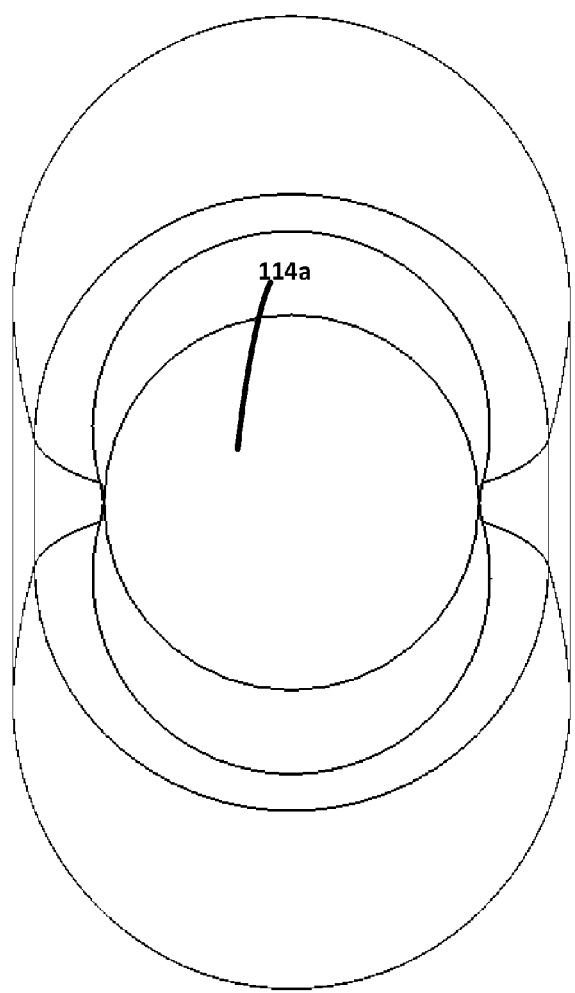
FIGS. 21A-B show a bottom view of the base of FIGS. 19A-B.
Figure 21B:
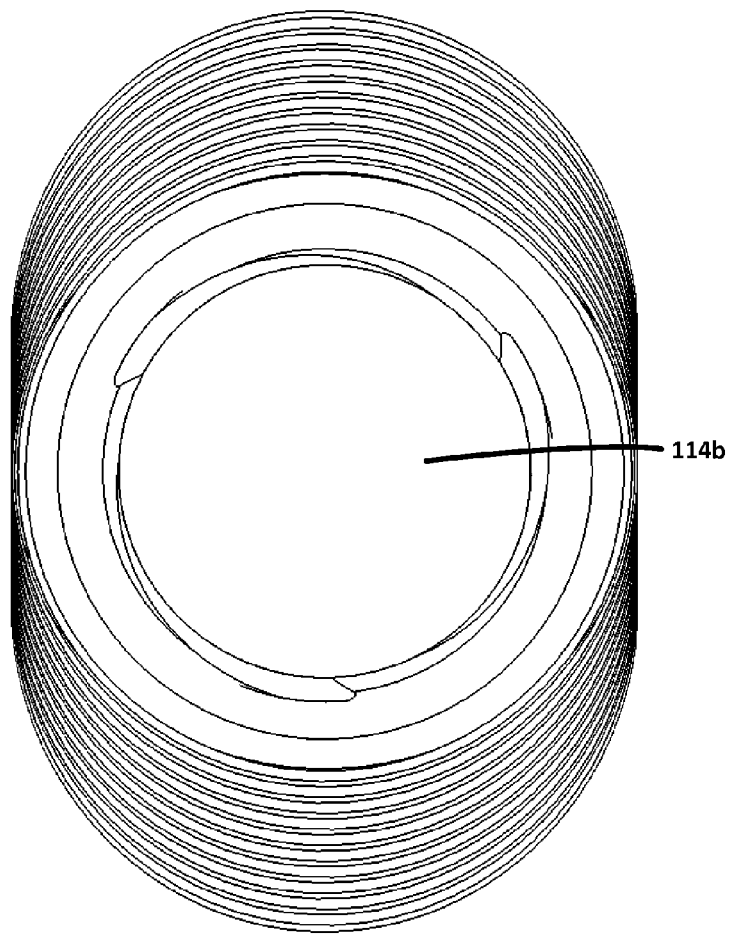

For instance, as shown in FIG. 19B, the base member 108 may be formed to exhibit external ridges 109. In general and in comparison with the base member 108 shape of the base member 108a as shown in FIG. 19A, the ridges 109 improve bone integration (increased surface area and distribution of stress/load). See also FIG. 8B. In some examples, the base member 108 may be formed of a zirconia or titanium material. In some examples, dimensions of the base member 108 may be in a range from about 2.0 millimeters to about 6.0 millimeters deep inclusive, and various combinations of dimensions at the rim ranging from about 4.0 millimeters to about 10.0 millimeters inclusive.

Figure 8A:
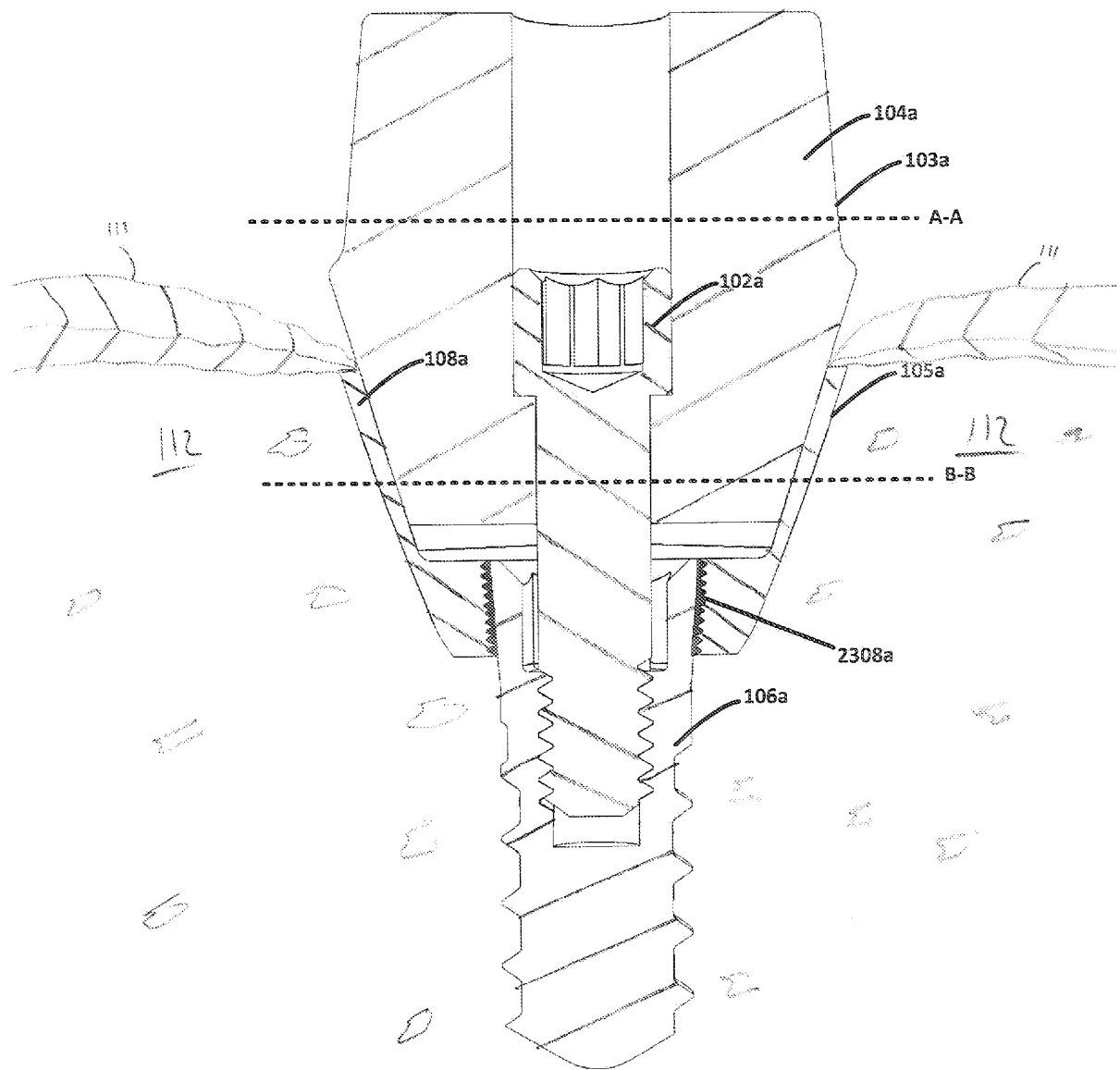
FIGS. 8A-B show a cross-section of the side view of FIGS. 7A-B.
Figure 8B:
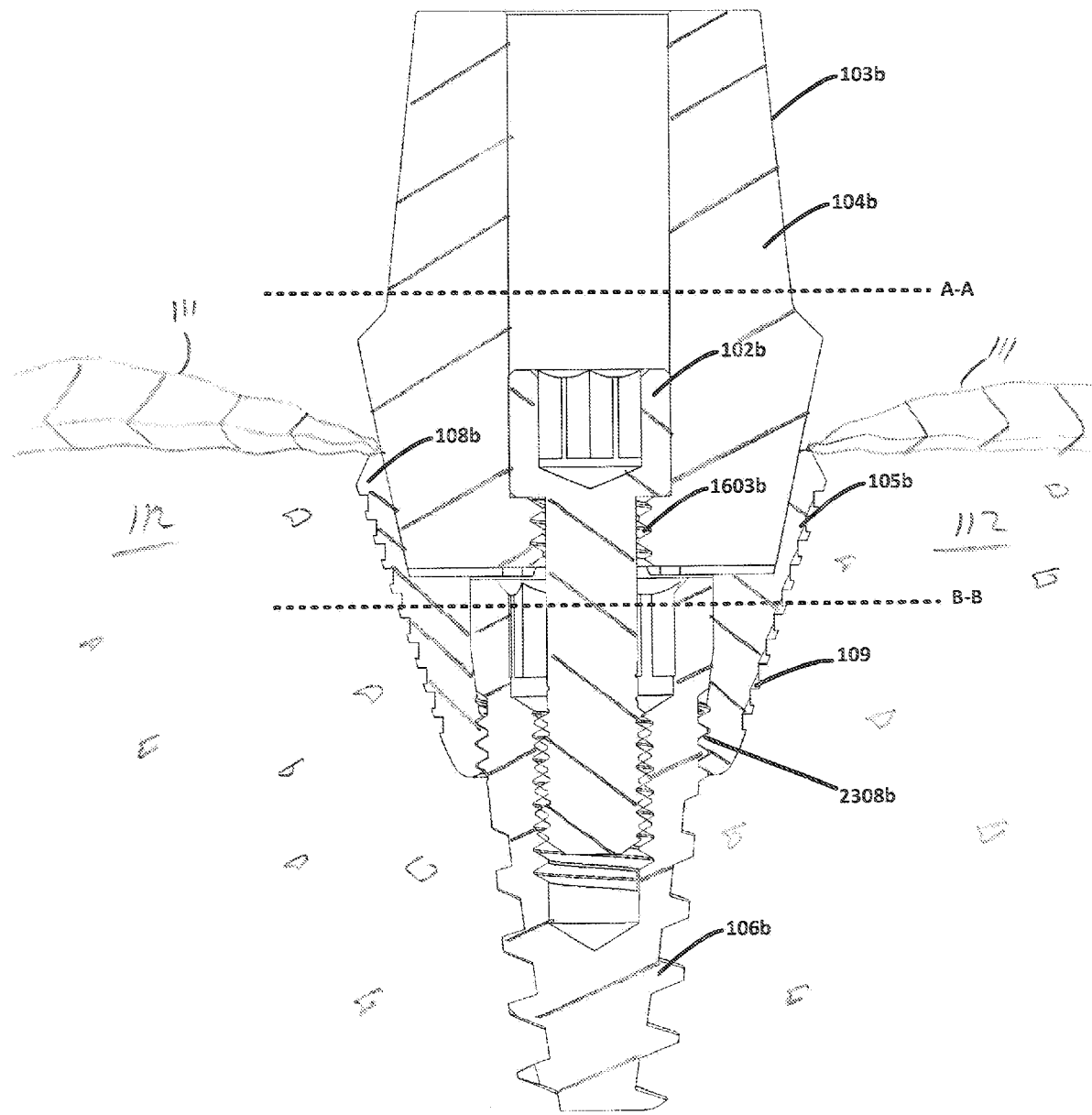

Referring now to FIGS. 23A-D, only the implant screw 106 is shown positioned to the base member 108. In particular, a side view 2302(a,b) along with a corresponding cross-section 2304(a,b) of the implant screw 106 positioned to the base member 108 is shown. As mentioned above, the base member 108 includes features that are complementary to external features of the head portion 1604 of the implant screw 106. In particular, an inner surface 2306(a,b) of the central passage 114 formed within the base member 108 includes a female thread 2308(a,b) that is complementary to the external thread 1614 of the head portion 1604 of the implant screw 106. The female thread 2308 is also shown in FIGS. 8A-B. The inner surface 2306 of the central passage 114 is further tapered in a manner that is complementary to the above-mentioned taper of the head portion 1604 of the implant screw 106. When the implant screw 106 is positioned to the base member 108 as shown in FIGS. 23A-D, a friction seal or cold weld is formed at the interface between female thread 2308 of the base member 108 and the external thread 1614 of the head portion 1604 so that the joining of the implant screw 106 to the base member 108 is achieved without fusion/heating at the mentioned interface of these two parts.

Figure 23A:
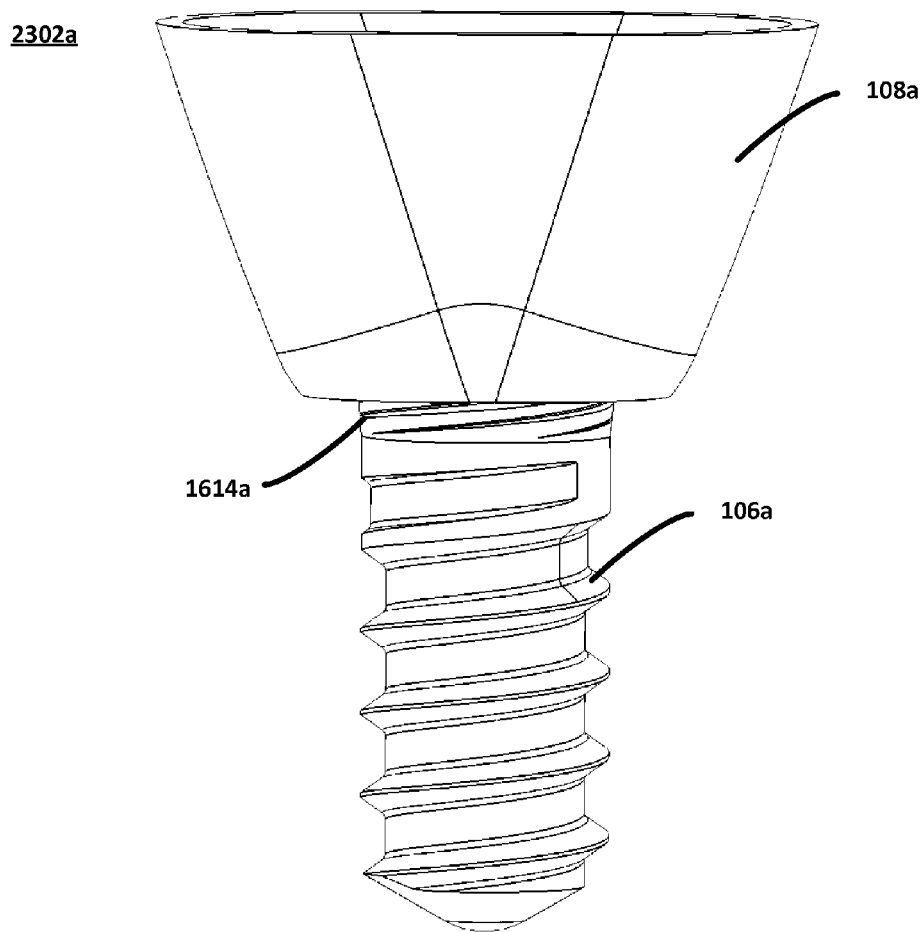
FIGS. 23A-D show other certain components of FIGS. 8A-B.
Figure 23B:
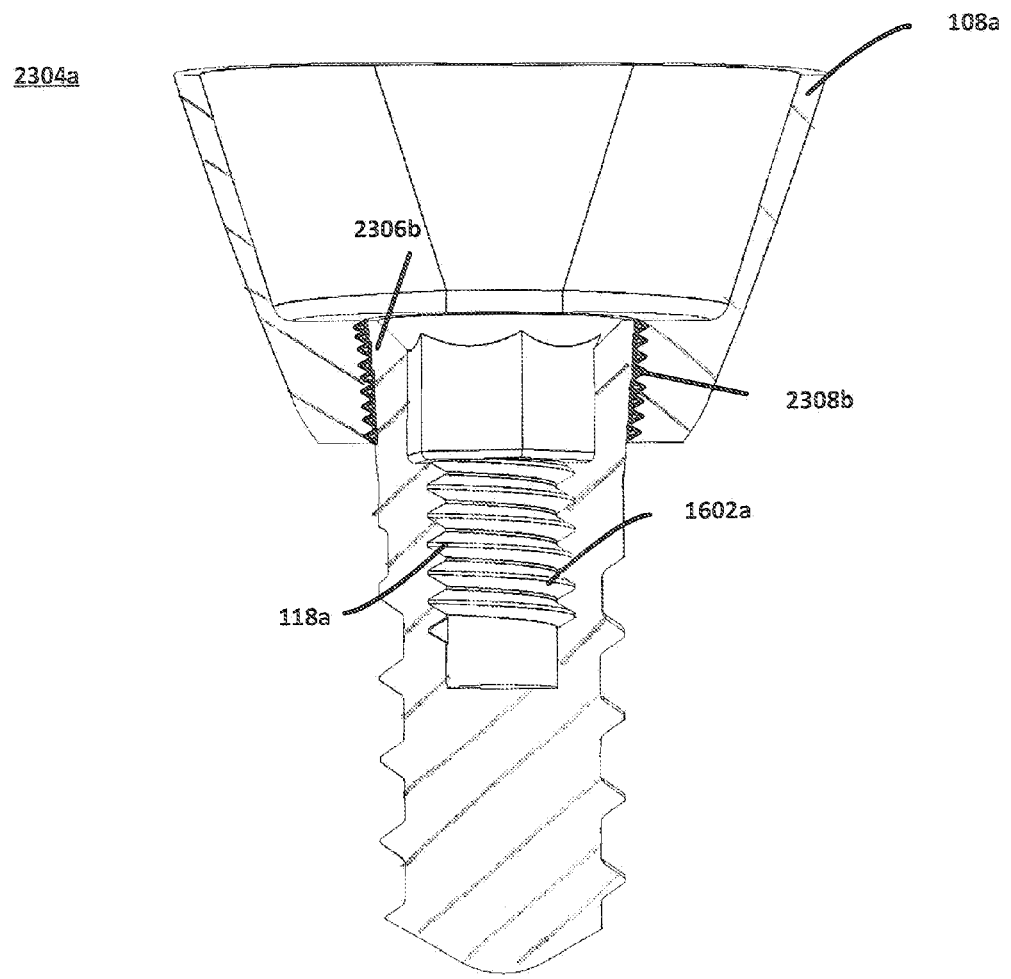
Figure 23C:
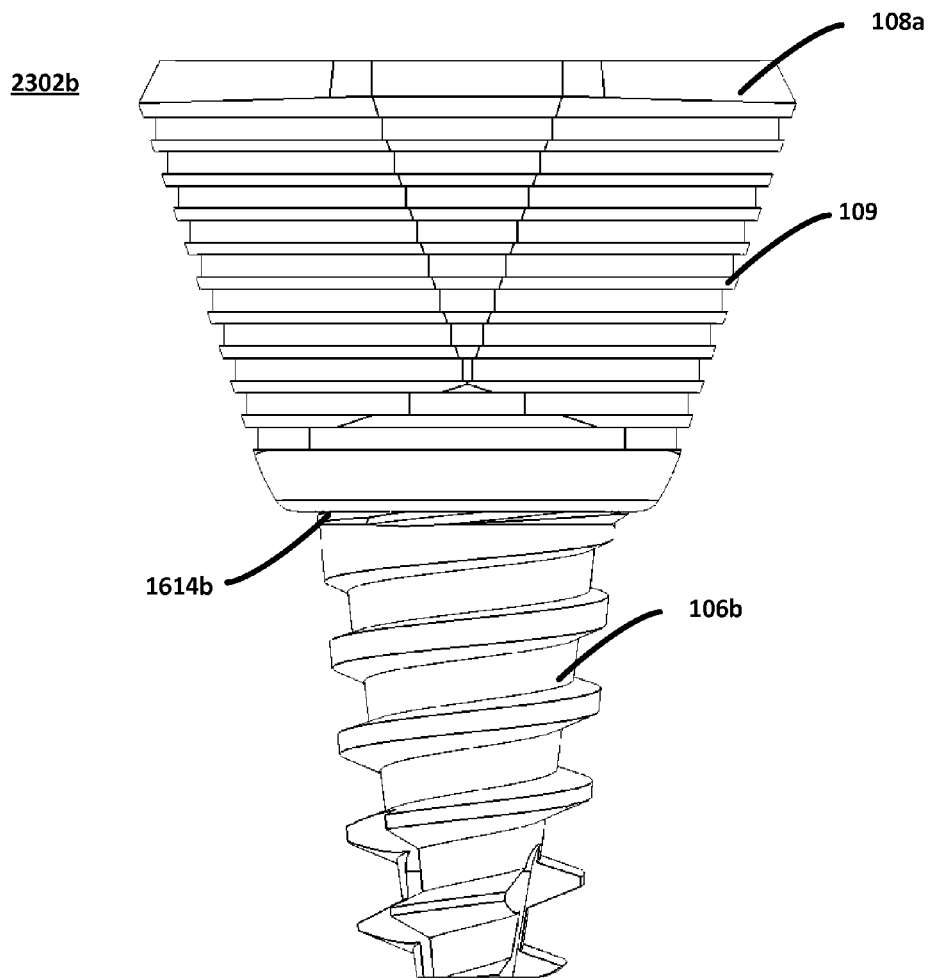
Figure 23D:
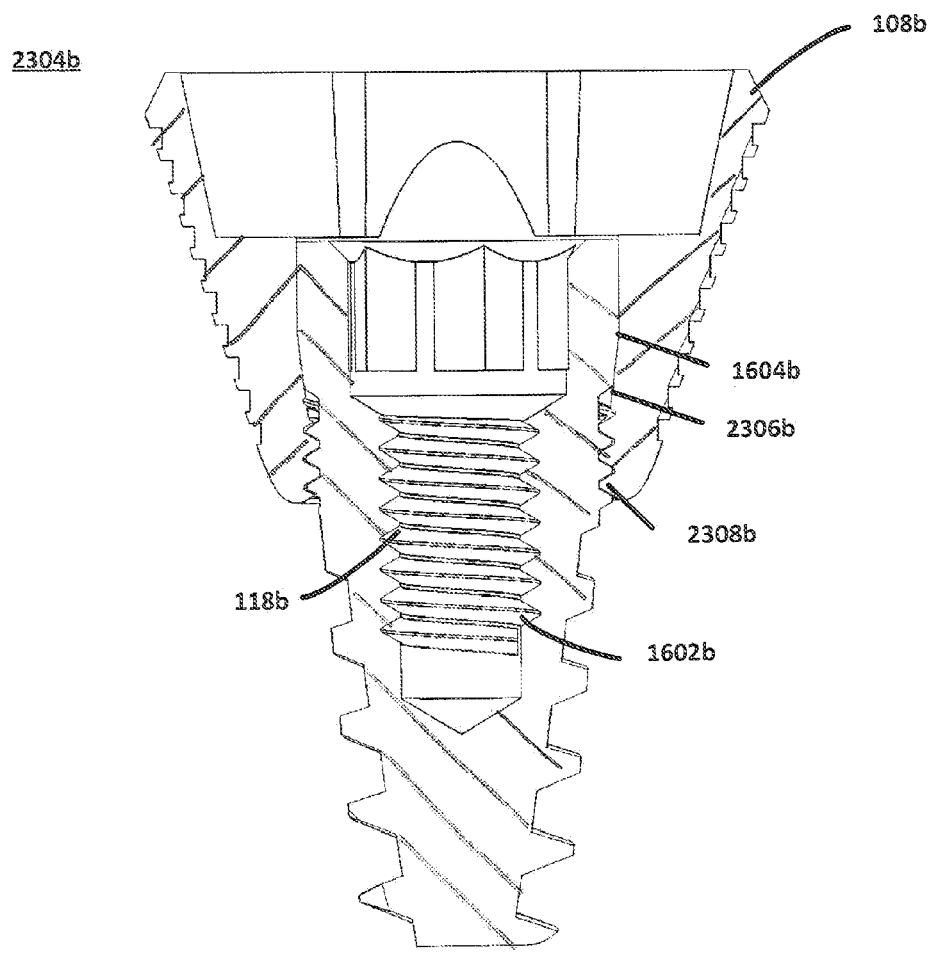

Referring still to FIGS. 23A-D, and as shown and discussed above in connection with FIGS. 16A-B, the external thread 1614a of the example implant screw 106a of FIG. 16A and FIGS. 23A-B is immediately adjacent to the top edge 1611a of the implant screw 106a, whereas the external thread 1614b of the example implant screw 106b of FIG. 16B and FIGS. 23C-D is offset from the top edge 1611b of the implant screw 106b. Therefore, one difference between the implant screw 106a and the implant screw 106b is at the head region near the keyed aperture 1610(a-b).

Specifically, with the implant screw 106a, the entire head portion 1604a (see FIG. 16A) exhibits the external thread 1614a that threads with the internal thread 2308a of the base member 108a, and the tapered head portion 1604a (that exhibits the external thread 1614a) is matched with the tapered inner surface 2306a of the central passage 114a of the base member 108a (that exhibits the internal thread 2308*a*) to form a friction fit or cold weld. Specifically, engagement of the external thread 1614*a* and the internal thread 2308*a* serves to maintain this friction fit or cold weld so that over time there is no micro-leakage of fluids between this interface. See also FIG. 8A and above discussion.

In contrast, with the implant screw 106*b*, the entire head portion 1604*b* (see FIG. 16*b*) does not exhibit the external thread 1614*b* that threads with the internal thread 2308*b* of the base member 108*a*. Only a portion of the head portion 1604*b* includes the external thread 1614*b*. Also, the external thread 1614*b* is not included on a tapered section of the head portion 1604*b* but on any straight, cylindrical section near or adjacent to tapered section 1613*b* as shown in FIG. 9B and FIG. 16B. Advantageously, and as mentioned in above, this is done to facilitate manufacturing of the implant screw 106 and the base member 108 because it is easier to manufacture threads on straight section, rather than tapered sections. However, the implant screw 106*b* still exhibits a tapered section to provide the friction fit or cold weld similar to the implant screw 106*a* of FIG. 9A for example. Further, the external thread 1614*b* may be placed above or below the tapered section 1613*b*, so long as that thread is able to thread with the thread 2308*a* of the base member 108*b* to form the friction fit or the cold weld.

Figure 24:
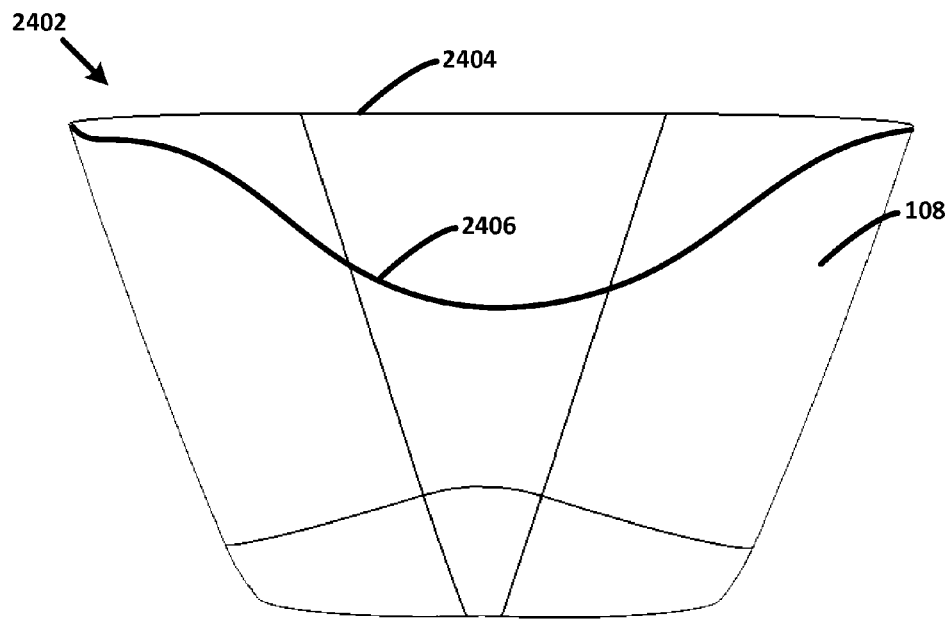
FIG. 24 shows a modification to the base of FIG. 19A.

Referring now to FIG. 24, a side view 2402 of the base member 108 is shown. In this example, a periphery 2404 of the base member 108 is shown as approximately or about flat when viewed from at least the side. Many other examples are possible. For example, the periphery 2404 of the base member 108 may be machined in situ or prior to implant so as to exhibit a non-flat shape when viewed from at least the side, as shown by periphery 2406 in FIG. 24. In this example, the top portion of the base member 108 appears saddle-shaped due to the shape of the periphery 2406. Many other examples are possible, where the profile of the top portion of the base member may be formed as desired, to exhibit an irregular shape for example that may be similar to the profile or shape of the gum line or bone line of a patient at or near the implant site.

Figure 25:
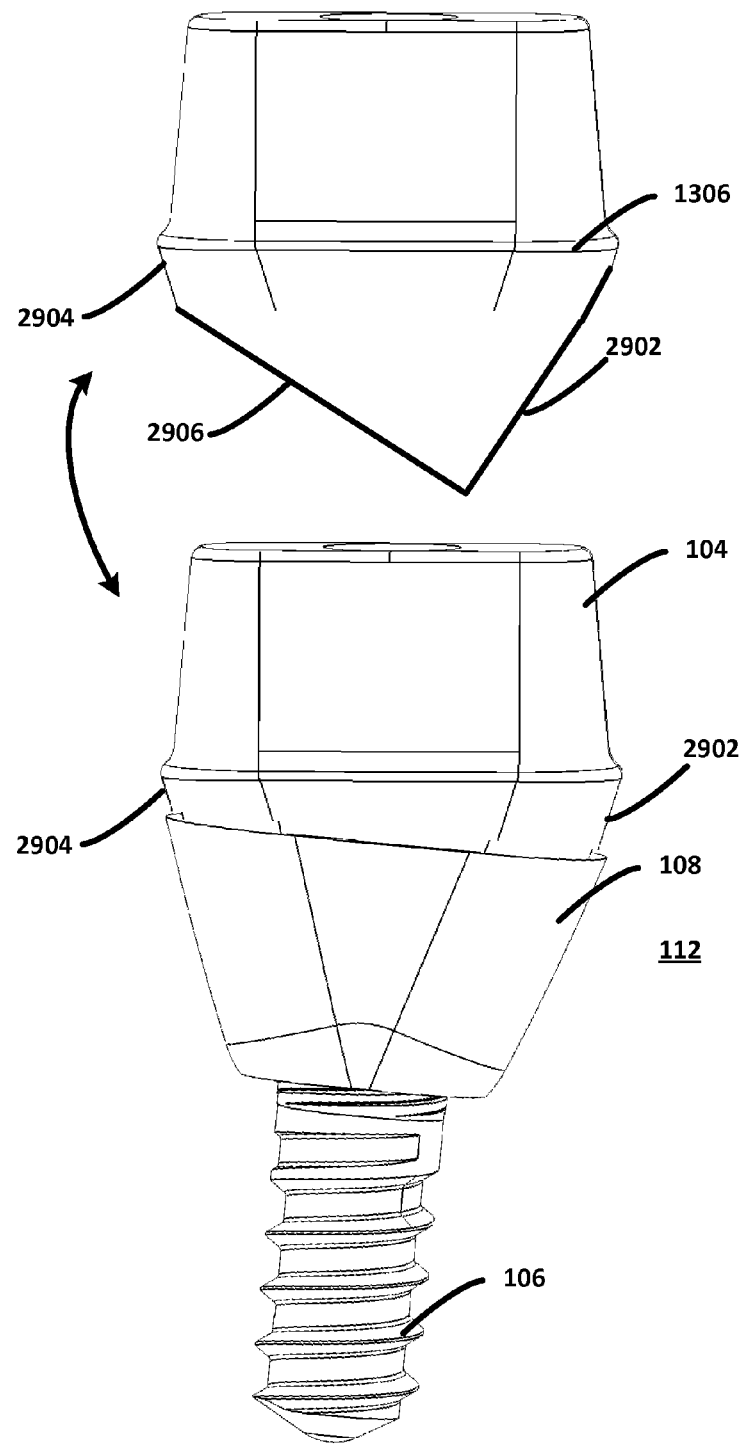
FIG. 25 shows a modification to the abutment of FIG. 13A.

Referring now to FIG. 25, a modification of the abutment member 104 is shown in accordance with the principles of the present disclosure. In particular, the abutment member 104 is formed to exhibit a long side 2902 and a short side 2904. Such an implementation may advantageously permit a crown (not shown) when positioned to the abutment member 104 to be orientated substantially "upright" in a desired position for aesthetic and/or practical (e.g., chewing) purposes. For example, as shown in FIG. 25, the base member 108 may be implanted to the jawbone 112 at an angle, due to the natural shape of the jawbone at the implant site or for some other reason. The irregular shape of the abutment member 104 may compensate for the angle exhibited by the base member 108 as shown in FIG. 25. It is contemplated that the abutment member 104 may be machined, molded, 3D printed, etc., to exhibit the irregular shape at time of implant (e.g., by machining bottom surface 2906), or may be selected from any of a number of different prefabricated abutment members formed to exhibit an irregular shape similar to that shown in FIG. 25.

As may be understood from the foregoing, a dental implant is disclosed whereby an eccentrically-shaped osteotomy cavity is formed in jawbone and then an eccentrically-shaped base member of the implant is positioned into the cavity. The base member serves as a platform to secure an eccentrically-shaped abutment member of the implant that in turn receives a dental restoration, such as a crown or denture. Advantageously, such an implementation may make it easy for a physician to slip the abutment member into the base member with a correct or proper orientation, and also prevent the abutment member from rotating with respect to the base member due to the complementary oblong or oval geometry of these pieces. Additionally, various features of the pieces or parts of the dental implant may improve bone integration and in general fit together with precision, and may in general be surface treated.

For example, the above-mentioned ridges 109 are optional but may serve to improve bone integration (increased surface area and distribution of stress/load). Also, surfaces or surface area in contact with bone, e.g., surface associated with ridges 109 and/or threads of the implant screw 106 may be surface treated, e.g., bead blasted, for the similar reason, namely to improve bone integration. This may be accomplished in a number of ways such as via additive like plasma spray, or subtractive like acid-wash or blasting). Furthermore, certain part mating areas such as between eccentric surfaces of the abutment member 104 and the base member 108, and surfaces between the base member 108 and implant screw 106, utilize a tapered angle so the parts may "cold weld" to tightly lock the pieces together. Advantageously, this may distribute forces more evenly across two pieces, and also create a seal at a joint to prevent bacterial micro-leakage.

Accordingly, a dental implant system or assembly and a method for implanting the same are contemplated and claimed and, although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims. Additionally, the methods, systems or assemblies as discussed above are examples. Various configurations may omit, substitute, or add various method steps or procedures, or components as appropriate. For instance, in alternative examples, the methods may be performed in an order different from that described, and/or various stages may be added, omitted, and/or combined.

What is claimed is:

1. A dental implant assembly, comprising:
    a base member adapted for placement into an opening in a patient's jawbone, wherein the base member includes a recess and a through-hole at a lower portion of the base member that extends from the recess through an end of the base member, and wherein the through-hole includes an internal screw thread that extends along a particular length of the through-hole;
    an implant screw adapted for insertion into the through-hole and jawbone, wherein the implant screw comprises an upper external screw thread to engage the internal screw thread of the through-hole, a lower external screw thread to engage the jawbone and to secure the base member in the opening, and a head portion comprising a receiver with an internal screw thread;
    an abutment member adapted for nested placement into the recess of the base member, wherein the abutment member includes an internal passage that extends between a top end and a bottom end, and wherein the bottom end exhibits a shape to mate with the recess of the base member; and
    a securing screw adapted for insertion into the internal passage of the abutment member and into the receiver of the head portion of the implant screw, wherein the securing screw includes an external screw thread to engage the internal screw thread of the head portion to secure the abutment member to the base member.

2. The dental implant assembly of claim 1, wherein the base member is basket-shaped and the recess is non-circular or eccentric in cross-section.

3. The dental implant assembly of claim 1, wherein the internal screw thread of the through-hole includes a plurality of individual internal screw threads.

4. The dental implant assembly of claim 1, wherein an external surface of the base member includes a plurality of concentric ridges.

5. The dental implant assembly of claim 1, wherein an external surface of the head portion of the implant screw is tapered to match a taper of the through-hole of the base member.

6. The dental implant assembly of claim 1, wherein a length of the implant screw along the separate external screw thread is tapered.

7. The dental implant assembly of claim 1, wherein pitch of the external screw thread to engage the internal screw thread of the through-hole is different than pitch of the separate external screw thread to engage jawbone to secure the base member in the opening.

8. The dental implant assembly of claim 1, wherein the lower external screw thread includes at least one leading and open edge.

9. The dental implant assembly of claim 1, wherein the abutment member is plug-shaped and an outer surface of the abutment member is non-circular or eccentric in cross-section.

10. The dental implant assembly of claim 1, wherein the internal passage of the abutment member includes an internal screw thread that is complementary to the external screw thread of the securing screw.

11. The dental implant assembly of claim 1, wherein a head portion of the securing screw includes a keyed-aperture and a plurality of torque-bearing surfaces.

12. The dental implant assembly of claim 1, wherein the base member is non-circular or eccentric in cross-section, and wherein the abutment member is non-circular or eccentric in cross-section.

13. A method of implanting a dental implant in a jawbone of a patient, comprising:
 positioning an eccentric base member of the dental implant into an eccentric osteotomy formed within the jawbone of the patient;
 inserting an end of an implant screw of the dental implant into an internal passage of the base member;
 applying torque to a head portion of the implant screw to engage a lower external screw thread of the implant screw to the jawbone to secure the base member to the osteotomy, and to engage an upper external screw thread of the implant screw with an internal screw thread of the internal passage of the base member;
 positioning an abutment member of the dental implant into a recess of the base member;
 inserting an end of a securing screw of the dental implant into an internal passage of the abutment member; and
 applying torque to a head portion of the securing screw, to engage an external screw thread of the securing screw with an internal screw thread of a head portion of the implant screw to secure the abutment member to the base member.

14. The method of claim 13, further comprising forming the eccentric osteotomy within the jawbone of the patient.

15. The method of claim 13, further comprising drilling a pilot hole into the jawbone to receive the end of the implant screw.

16. The method of claim 13, further comprising securing a dental restoration component to the abutment member.

17. The method of claim 13, further comprising modifying a shape of the base member to conform to a feature of the jawbone or jaw of the individual.

18. The method of claim 13, further comprising modifying a shape of the base member to compensate for a feature of the jawbone or jaw of the individual.

19. The method of claim 13, wherein the base member is non-circular or eccentric in cross-section, and wherein the abutment member is non-circular or eccentric in cross-section.

20. A dental implant assembly, comprising:
 a base member, wherein the base member includes a recess and a passage that extends from the recess through an end of the base member, and wherein the passage includes an internal screw thread that extends along a particular length of the passage;
 an implant screw, wherein the implant screw includes an external screw thread to engage the internal screw thread of the passage and a separate external screw thread to engage a patient's jawbone to secure the base member in an osteotomy cavity when positioned thereto; and
 an abutment member, wherein the abutment member includes an internal passage that extends between a top end and a bottom end of the abutment member, and wherein the bottom end exhibits a shape matched with a shape of the recess of the base member.

21. The dental implant assembly of claim 20, further comprising:
 a securing screw, wherein the securing screw includes an external screw thread to engage an internal screw thread of a head portion of the implant screw to secure the abutment member to the base member.

* * * * *